United States Patent
Skerra et al.

(10) Patent No.: US 10,920,255 B2
(45) Date of Patent: Feb. 16, 2021

(54) PROCESS FOR PRODUCING L-METHIONINE FROM METHIONAL

(71) Applicant: Evonik Operations GmbH, Essen (DE)

(72) Inventors: Arne Skerra, Dachau (DE); Lukas Eisoldt, Freising (DE)

(73) Assignee: Evonik Operations GmbH, Essen (DE)

( * ) Notice: Subject to any disclaimer, the term of this patent is extended or adjusted under 35 U.S.C. 154(b) by 44 days.

(21) Appl. No.: 16/466,337

(22) PCT Filed: Nov. 30, 2017

(86) PCT No.: PCT/EP2017/080961
§ 371 (c)(1),
(2) Date: Jun. 4, 2019

(87) PCT Pub. No.: WO2018/104143
PCT Pub. Date: Jun. 14, 2018

(65) Prior Publication Data
US 2019/0338324 A1    Nov. 7, 2019

(30) Foreign Application Priority Data

Dec. 5, 2016 (EP) ..................................... 16202157

(51) Int. Cl.
| | | |
|---|---|---|
| *C12P 13/12* | (2006.01) | |
| *C12Q 1/527* | (2006.01) | |
| *C12Q 1/32* | (2006.01) | |
| *C12Q 1/52* | (2006.01) | |
| *C12P 13/06* | (2006.01) | |
| *C12P 13/08* | (2006.01) | |
| *C12P 13/22* | (2006.01) | |
| *A61K 38/00* | (2006.01) | |

(52) U.S. Cl.
CPC .............. *C12P 13/12* (2013.01); *C12P 13/06* (2013.01); *C12P 13/08* (2013.01); *C12P 13/222* (2013.01); *C12Y 102/02001* (2013.01); *C12Y 104/0102* (2013.01); *C12Y 104/01009* (2013.01); *C12Y 206/01057* (2013.01); *C12Y 206/01088* (2013.01); *C12Y 401/01001* (2013.01); *C12Y 401/01043* (2013.01); *C12Y 401/01072* (2013.01)

(58) Field of Classification Search
CPC combination set(s) only.
See application file for complete search history.

(56) References Cited

U.S. PATENT DOCUMENTS

| | | | |
|---|---|---|---|
| 4,304,858 A | 12/1981 | Wandrey et al. | |
| 5,770,769 A | 6/1998 | Geiger et al. | |
| 10,815,508 B2 * | 10/2020 | Skerra ..................... | C12P 11/00 |
| 2003/0138524 A1 * | 7/2003 | Cecava ................... | A23K 50/10 |
| | | | 426/74 |
| 2008/0274518 A1 * | 11/2008 | Hicks ...................... | C12P 17/10 |
| | | | 435/121 |
| 2011/0217734 A1 * | 9/2011 | Metcalf .................... | C12P 21/06 |
| | | | 435/69.1 |
| 2013/0273616 A1 * | 10/2013 | Hicks ...................... | C12P 17/10 |
| | | | 435/121 |
| 2015/0064750 A1 * | 3/2015 | Osterhout ................ | C12P 7/62 |
| | | | 435/135 |
| 2015/0111260 A1 * | 4/2015 | Burke ..................... | C12N 9/88 |
| | | | 435/106 |
| 2015/0152440 A1 * | 6/2015 | Garcez Lopes .......... | C12P 7/18 |
| | | | 435/158 |
| 2015/0284749 A1 * | 10/2015 | Cabirol ................ | C12N 9/0004 |
| | | | 435/116 |
| 2015/0322441 A1 * | 11/2015 | Baynes .................... | C12P 7/62 |
| | | | 435/128 |
| 2016/0251643 A1 * | 9/2016 | Weiner ................. | C12N 9/1022 |
| | | | 435/232 |
| 2017/0232043 A1 * | 8/2017 | Falb ...................... | A61K 9/0019 |
| | | | 424/93.2 |

FOREIGN PATENT DOCUMENTS

| | | |
|---|---|---|
| EP | 0 023 346 | 2/1981 |
| EP | 3 168 301 | 5/2017 |
| GB | 2 161 159 | 1/1986 |
| WO | 2005/121068 | 12/2005 |
| WO | 2005/121079 | 12/2005 |
| WO | 2008/013432 | 1/2008 |
| WO | 2012/091479 | 7/2012 |

(Continued)

OTHER PUBLICATIONS

Liu et al. (2010) Methanococci Use the Diaminopimelate Aminotransferase (DapL) Pathway for Lysine Biosynthesis, J. Bacteriol., vol. 192, pp. 3304-3310.*
Kim et al. (2006) Characterization of a Gene Encoding Diaminopimelate Decarboxylase from Rice(, ntegr. Biosci., vol. 10, pp. 197-201.*
Amarita et al. (2001) Conversion of methionine to methional by Lactococcus lactis, FEMS Microbiol., vol. 204, pp. 189-195.*
Ishii et al. (2004) Reversible and nonoxidative c-resorcylic acid decarboxylase: characterization and gene cloning of a novel enzyme catalyzing carboxylation of resorcinol, 1,3-dihydroxybenzene, from Rhizobium radiobacterBiochem. Biophys. Res. Commun., vol. 324, pp. 611-620.*
International Search Report dated Feb. 5, 2018 in PCT/EP2017/080961.
Written Opinion dated Feb. 5, 2018 in PCT/EP2017/080961.

(Continued)

*Primary Examiner* — Scarlett Y Goon
*Assistant Examiner* — Samuel W Liu
(74) *Attorney, Agent, or Firm* — Grüneberg and Myers PLLC

(57) ABSTRACT

A method is useful for the biocatalytic synthesis of proteinogenic L-amino acids, such as L-alanine, L-valine, L-methionine, L-leucine, L-isoleucine or L-phenylalanine from a respective aldehyde and carbon dioxide. In particular, the method is useful for the biocatalytic synthesis of L-methionine from 3-methylthio-propanal ("methional") and carbon dioxide.

6 Claims, 8 Drawing Sheets

Specification includes a Sequence Listing.

(56) References Cited

FOREIGN PATENT DOCUMENTS

WO 2016/006521 1/2016

OTHER PUBLICATIONS

Miyazaki et al., "Enzymatic synthesis of pyruvic acid from acetaldehyde and carbon dioxide", Chem. Commun., 2001, 1800-1801 DOI: 10.1039/b104873m XP-001100088.

Sekowska et al., "The methionine salvage pathway in Bacillus subtilis", BMC Microbiology 2002, 2:8, 14 pages, XP 21014825A, DOI: 10.1186/1471-2180-2-8.

Tong et al., "Enzymatic Synthesis of $_L$-Lactic Acid From Carbon Dioxide and Ethanol With an Inherent Cofactor Regeneration Cycle," Biotechnology and Bioengineering, vol. 108, No. 2, Feb. 2011, 465-469 DOI 10.1002/bit.22938.

Wchmann et al., "Continuous Enzymatic Transformation in an Enzyme Membrane Reactor with Simultaneous NAD(H) Regeneration," Biotechnology and Bioengineering, vol. XXIII, pp. 2789-2802 (1981).

T. Willke, "Methionine production-a critical review," Appl Microbiol Biotechnol (2014) 98: 9893-9914 DOI 10.1007/s00253-014-6156-y.

Bulfer et al., "Crystal structure of Saccharomyces cerevisiae Aro8, a putative α-aminoadipate aminotransferase," Protein Science 2013, vol. 22: 1417-1424 DOI: 10.1002/pro.2315.

Dolzan et al., "Crystal structure and reactivity of YbdL from Escherichia coli identify a methionine aminotransferase function," FEBS Letters 571 (2004) 141-146 doi: 10.1016/j.febslet.2004.06.075.

Egorov et al., "NAD-Dependent Formate Dehydrogenase from Methylotrophic Bacterium, Strain 1," Eur. J. Biochem. 99, 569-576 (1979).

Killenberg-Jabs et al., "Role of Glu51 for Cofactor Binding and Catalytic Activity in Pyruvate Decarboxylase from Yeast Studied by Site-Directed Mutagenesis," Biochemistry 1997, 36, 1900-1905.

Kneen et al., "Characterization of a thiamin diphosphate-dependent phenylpyruvate decarboxylase from Saccharomyces cerevisiae," FEBS Journal 278 (2011) 1842-1853 doi: 10.1111/j.1742-4658.2011.08103.x.

Li et al., "Cloning, Protein Sequence Clarification, and Substrate Specificity of a Leucine Dehydrogenase from Bacillus sphaericus ATCC4525," Appl Biochem Biotechnol (2009) 158: 343-351 DOI: 10.1007/s12010-008-8304-2.

Schütte et al., "Purification and Properties of Formaldehyde Dehydrogenase and Formate Dehydrogenase from Candida boidinii," Eur. J. Biochem. 62, 151-160 (1976).

A. Skerra, "Use of the tetracycline promoter for the tightly regulated production of a murine antibody fragment in Escherichia coli," Gene, 151 (1994) 131-135.

Studier et al., "Use of Bacteriophage T7 RNA Polymerase to Direct Selective High-level Expression of Cloned Genes," J. Mol. Biol. (1986) 189, 113-130.

Takada et al., "Thermostable Phenylalanine Dehydrogenase of Thermoactinomyces intermedius: Cloning, Expression, and Sequencing of Its Gene," J. Biochem. 109, 371-376 (1991).

Yep et al., "Determinants of substrate specificity in KdcA, a thiamin diphosphate-dependent decarboxylase," Bioorganic Chemistry 34 (2006) 325-336 doi:10.1016/j.bioorg.2006.08.005.

* cited by examiner

PROCESS FOR PRODUCING L-METHIONINE FROM METHIONAL

This application is a National Stage entry under § 371 of international Application No. PCT/EP2017/080961, filed on Nov. 30, 2017, and which claims the benefit of European Application No. 16202157.0, filed on Dec. 5, 2016, all of which are incorporated by reference in their entirety.

The present invention relates to a method for the biocatalytic synthesis of proteinogenic L-amino acids, such as L-alanine, L-valine, L-methionine, L-leucine, L-isoleucine or L-phenylalanine from a respective aldehyde and carbon dioxide as well as an amino donor and, in particular, L-methionine from 3-methylthio-propanal ("methional") and carbon dioxide as well as an amino donor such as ammonia.

α-Amino acids are usually synthesized by the Strecker amino acid synthesis which involves the treatment of an aldehyde with potassium cyanide and ammonia leading to an α-amino nitrile as an intermediate. Hydrolysis of the nitrile into acid then yields the α-amino acid. This chemical synthesis gives a racemic mixture of D- and L-amino acids. Proteinogenic α-amino acids may also be produced by fermentation of microorganisms leading preferentially to L-amino acids.

The amino acid methionine is currently industrially produced worldwide in large amounts and is of considerable commercial importance. Methionine is employed in many fields, such as pharmaceutical, health and fitness products, but particularly as additive in many feedstuffs for various livestock, where both the racemic and the enantiomerically pure L-stereoisomer of methionine may be used.

At the industrial scale, methionine is produced chemically via the Bucherer-Bergs reaction, which is a variant of the Strecker synthesis. The starting substance, 3-methylthio-propanal ("methional"), is usually prepared from propenal (acrolein) and methanethiol (methyl mercaptan). Methional, hydrogen cyanide, ammonia and carbon dioxide are reacted to give 5-(2-methylmercaptoethyl) hydantoin, which is subsequently hydrolyzed by alkali to give the alkali metal D,L-methionate. The D,L-methionine is then liberated by neutralization with acid (U.S. Pat. No. 5,770,769). However, the need to use hydrogen cyanide is a disadvantage of this process. Owing to the high toxicity of hydrogen cyanide, outlay on safety must be high for the reaction. Another great disadvantage are the high amounts of ammonium sulfate that is formed by purification of the hydrogen cyanide with sulfuric acid prior to its use for methionine hydantoin synthesis. There is therefore a need for an HCN-free process for the production of methionine.

Various other methods can also be used to prepare methionine, for example, the amidocarbonylation of methional in the presence of an amide, carbon monoxide and of a transition metal carbonyl catalyst (WO 2005/121068 A1, WO 2005/121079 A1), the hydrolysis of proteins or the fermentation of microorganisms producing methionine.

As mentioned above, in chemical synthesis, like all other α-amino acids, methionine usually is produced as a racemic mixture of D- and L-methionine. However, pharmaceutical or medical applications often require the chiral pure L-amino acid, in particular L-methionine. L-Methionine may be produced either by conversion of the D,L-racemate into pure enantiomers or by fermentation of suitable microorganisms. However, a major drawback of the complete fermentation of L-methionine in microorganisms is the huge amount of nutrients and/or energy required, in particular for the reduction of sulfur to be introduced into the methionine molecule, which is usually added in the form of sulfate to the fermentation media due to the toxic effects of reduced sulfur compounds (such as methanethiol) on the methionine-producing microorganisms. Whereas the direct synthesis of L-methionine starting from aspartate requires 1 ATP and 2 NADPH molecules, the incorporation of sulfur from inorganic sulfate additionally consumes 2 ATP, 1 GTP and 4 NADPH molecules. Therefore, the energy balance would be tremendously improved if a reduced sulfur compound (e.g. methanethiol) could be used for the L-methionine synthesis (Wilke (2014) Appl. Microbiol. Biotechnol. 98, 9893-9914).

To solve this problem, a two-stage biotechnological method for preparing L-methionine was proposed by Kim et al. (WO 2008/013432 A1). In a first step, an L-methionine precursor, O-succinyl-L-homoserine or O-acetyl-L-homoserine, is obtained by means of recombinant microorganisms and accumulated in the culture broth. In the second step, the L-methionine precursor is reacted with methanethiol in the presence of a protein having O-succinyl-L-homoserine sulfhydrylase activity or O-acetyl-L-homoserine sulfhydrylase activity to give L-methionine and the corresponding carboxylic acid, i.e. acetate or succinate. However, in this enzymatic reaction, equimolar amounts of acetate or succinate are formed in addition to L-methionine. When choosing O-acetyl-L-homoserine as L-methionine precursor, for example, this leads to high acetate concentration in the course of the reaction, particularly at industrial scale. However, acetate cannot be completely removed from the L-methionine product with acceptable effort. Accordingly, Hong et al. (WO 2012/091479 A2) proposed numerous methods to remove and to reuse the relatively large amounts of acetate generated in the second stage of the L-methionine production process from the L-methionine product.

Several attempts have been undertaken to use carbon dioxide as C1 building block for carbon chain extension. Miyazaki et al. (Chem. Commun., 2001, 1800-1801) reported the successful synthesis of pyruvic acid from acetaldehyde in the presence of pyruvate decarboxylase and carbon dioxide as C1 building block making use of the reverse enzymatic reaction. The reaction requires a large excess of carbon dioxide in order to drive the equilibrium into the opposite direction of decarboxylation. A multienzyme catalytic system including a cofactor regeneration cycle that uses carbon dioxide and ethanol to produce L-lactate via acetaldehyde and pyruvic acid was proposed by Tong et al. (Biotechnol. Bioeng. (2011) 108, 465-469).

Wichmann et al. (Biotechnol. Bioeng. (1981) 23, 2789-2802) proposed for the reductive amination of 2-oxo-4-methylpentanoic acid (α-ketoisocaproate) to L-leucine catalyzed by L-leucine dehydrogenase (LeuDH), an NADH-dependent enzyme, a biocatalytic NADH regeneration system using formate and formate dehydrogenase for the regeneration of NADH.

The object of the present invention is to provide a method for producing L-amino acids, such as L-alanine, L-valine, L-methionine, L-leucine, L-isoleucine and L-phenylalanine that uses carbon dioxide instead of cyanide as C1 building block and thus avoids the formation of high amounts of ammonium sulfate and that directly leads to the enantiomerically pure L-amino acid.

This object is achieved by a method for producing an L-amino acid, comprising a step of reacting a mixture comprising an aldehyde, carbon dioxide, a decarboxylase, its corresponding cofactor and (a) at least one donor amino acid and an aminotransferase and/or (b) NADH, ammonia and/or an ammonium salt and an amino acid dehydrogenase to form the L-amino acid or a salt thereof.

Preferred L-amino acids that can be synthesized from their starting aldehydes by the method according to the present invention are L-alanine from ethanal (acetaldehyde), L-valine from 2-methyl propanal, L-methionine from 3-(methylthio) propanal (methional), L-leucine from 3-methyl butanal, L-isoleucine from 2-methyl butanal and L-phenylalanine from 2-phenyl ethanal (phenyl acetaldehyde).

In a preferred embodiment of the present invention, the object is achieved by a method for producing L-methionine (L-Met), comprising a step of reacting a mixture of 3-(methylthio)-propanal (methional), carbon dioxide, a decarboxylase, its corresponding cofactor and (a) at least one donor amino acid and an aminotransferase and/or (b) NADH, ammonia and/or an ammonium salt and an amino acid dehydrogenase to form L-methionine or a salt thereof.

Without willing to be bound by theory, it is thought that, initially, the decarboxylase in the mixture catalyzes its reverse reaction, i.e. the carboxylation of the aldehyde, e.g. methional, with carbon dioxide ($CO_2$), which leads to the intermediate α-keto acid (2-oxo acid), e.g. 4-methylthio-2-oxobutanoic acid (MTOB). Subsequently, the α-carbonyl group of the α-keto acid, e.g. 2-MTOB, is exchanged by an amino group in a stereospecific reaction catalyzed by an aminotransferase to yield the L-amino acid, such as L-methionine (FIG. 1A). This reaction requires the presence of a donor amino acid (e.g. L-glutamine) which itself is converted to the respective α-keto acid. Alternatively, the conversion of the α-keto acid of said L-amino acid, e.g. MTOB, ity (Table 1). The carbon dioxide is preferably applied to the reaction mixture at a pressure from 10 to 7400 kPa (from 0.1 to 74 bar), preferably from 100 to 1000 kPa (1 to 10 bar), more preferable from 200 to 800 kPa (2 to 8 bar).

Aminotransferases that are particularly suitable for variant (a) of the method according to the present invention, e.g. the transfer of the amino group from the donor amino acid to the α-carbonyl group of MTOB, are, for example, the methionine aminotransferase YbdL, which originates from *E. coli*, and the aromatic aminotransferase Aro8, which originates from *Saccharomyces cerevisiae*, as well as mutants and variants of these aminotransferases having aminotransferase activity (Table 1). Preferably, the donor amino acid is different from the L-amino acid to be formed. Preferred donor amino acids for this variant of the method according to the present invention are at least one L-amino acid, selected from the group consisting of L-glutamine, L-glutamate, L-alanine, L-phenylalanine, L-tyrosine, L-leucine, L-isoleucine, L-histidine and L-tryptophan.

Amino acid dehydrogenases that are particularly suitable for variant (b) of the method according to the present invention, e.g. the reductive amination of MTOB formed from methional under the consumption of NADH and $NH_3$, are, for example, the leucine dehydrogenase LeuDH, which originates from *Bacillus sphaericus*, and the phenylalanine dehydrogenase PheDH, which originates from *Thermoactinomyces intermedius*, as well as well as mutants and variants of these amino acid dehydrogenases having amino acid dehydrogenase activity (Table 1).

TABLE 1

Enzymes suitable for the synthesis of L-Methionine from Methional.

| Enzyme class and example | Organism | Modifications | SEQ ID No. | Reaction |
|---|---|---|---|---|
| Decarboxylase EC 4.1.1 | | | | |
| Pyruvate decarboxylase: Pdc1 (P06169; Killenberg-Jabs et al. (1997) Biochemistry 36, 1900-1905) | *Saccharomyces cerevisiae* | C-terminal $His_6$-tag | 1 | Carboxylation of methional to MTOB |
| Phenylpyruvate decarboxylase: Aro10 (Q06408; Kneen et al. (2011) FEBS J. 278, 1842-1853) | *Saccharomyces cerevisiae* | ΔK635; C-terminal $His_6$-tag | 3 | |
| Branched chain decarboxylase: KdcA (Q6QBS4; Yep et al. (2006) Bioorg. Chem. 34, 325-336) | *Lactococcus lactis* | C-terminal $His_6$-tag | 5 | |
| Aminotransferase 2.6.1.87 & .6.1.57 | | | | |
| Methionine aminotransferase: YbdL (P77806; Dolzan et al. (2004) FEBS Lett. 571, 141-146) | *Escherichia coli* K12 MG1655 | N-terminal $His_6$-tag | 7 | Transamination of MTOB to L-Met |
| Aromatic aminotransferase: Aro8 from (P53090; Bulfer et al. (2013) Protein Sci. 22, 1417-1424) | *Saccharomyces cervisiae* | N-terminal $His_6$-tag | 9 | Transamination of MTOB to L-Met |
| Amino Acid dehydrogenase EC 1.4.1.9 | | | | |
| Leucine dehydrogenase: LeuDH (Li et al. (2009) Appl. Biochem. Biotechnol. 158, 343-351) | *Bacillus sphaericus* | N-terminal $His_6$-tag | 11 | Reductive amination of MTOB to L-Met |
| Phenylalanine dehydrogenase: PheDH (P22823; Takada et al. (1991) J. Biochem. 109, 371-376) | *Thermoactinomyces intermedius* | N-terminal $His_6$-tag | 13 | | to L-methionine, can be achieved by an amino acid dehydrogenase (e.g. LeuDH or phenylalanine dehydrogenase, PheDH) that catalyzes the reductive amination of the α-keto acid, e.g. of MTOB, under the consumption of NADH with $NH_3$ as amino donor (FIG. 1B).

The cofactor of the decarboxylase comprises thiamine pyrophosphate. Suitable decarboxylases that catalyze the carboxylation of methional with $CO_2$ are, for example, the pyruvate decarboxylase PDC1, which originates from *Saccharomyces cerevisiae*, the phenylpyruvate decarboxylase ARO10, which originates from *Saccharomyces cerevisiae*, and the branched chain decarboxylase KdcA, which originates from *Lactococcus lactis*, as well as mutants and variants of these decarboxylase having decarboxylase activ- Without willing to be bound by theory, during the two-step enzymatic synthesis of the L-amino acid from an aldehyde, such as L-methionine from methional, catalyzed by a decarboxylase (e.g. ARO10 or KdcA) and an amino acid dehydrogenase (e.g. LeuDH or PheDH) the cosubstrate NADH is consumed by the dehydrogenase for reduction of the α-carbonyl group of the α-keto acid, e.g. MTOB.

In order to recycle NADH from its oxidized form $NAD^+$ in situ, a formate dehydrogenase (e.g. CboFDH(C23A/F285S)) can be employed (FIG. 1C). This enzyme oxidizes formate with $NAD^+$ to yield $CO_2$, which may also serve as substrate for the carboxylation reaction of the aldehyde, e.g methional, as well as the cosubstrate NADH (Schotte et al.

(1976) Eur. J. Biochem. 62, 151-160; Wichmann et al. (1981) Biotechnol. Bioeng. 23, 2789-2802).

Therefore, in a particular embodiment of the method according to the present invention the reaction mixture comprising an aldehyde, carbon dioxide, a decarboxylase, its corresponding cofactor and NADH, ammonia and/or an ammonium salt and an amino acid dehydrogenase and, optionally, at least one donor amino acid and an aminotransferase, further comprises formic acid or a salt thereof and a formate dehydrogenase.

NADH regeneration can be achieved, for example, by a formate dehydrogenase, such as PseFDH from *Pseudomonas* sp. 101 (Egorov et al. (1979) Eur. J. Biochem. 99, 569-576) or formate dehydrogenase from *Candida boidinii* (CboFDH; 013437; Schotte et al. (1976) Eur. J. Biochem. 62, 151-160) or its mutant CboFDH(C23A/F285S), under consumption of formate and release of $CO_2$.

Therefore, in a preferred embodiment of the method according to the present invention the formate dehydrogenase originates from *Pseudomonas* sp. or from *Candida* sp., as well as mutants and variants of these formate dehydrogenases having formate dehydrogenase activity.

EXAMPLES

Figure 1A:
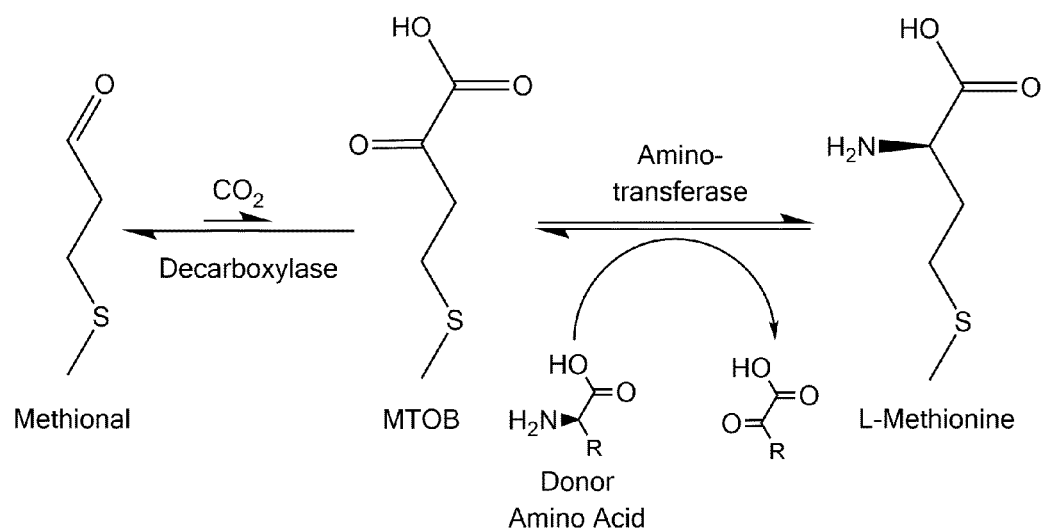
FIG. 1A: Scheme for the two-step biocatalytic synthesis of L-methionine from 3-(methylthio)propanal (methional) involving a decarboxylase and an aminotransferase.

Example 1: Production of Decarboxylases in *E. coli*

The gene for a pyruvate decarboxylase (Pdc1; SEQ ID NO: 1; P06169; Killenberg-Jabs et al. (1997) Biochemistry 36, 1900-1905) and a phenylpyruvate decarboxylase (Aro10; SEQ ID NO: 3; Q06408; Kneen et al. (2011) FEBS J. 278, 1842-1853), both from *Saccharomyces cerevisiae*, as well as the gene for a branched chain decarboxylase (KdcA) from *Lactococcus lactis* (SEQ ID NO: 5; Q6QBS4; Yep et al. (2006) Bioorg. Chem. 34, 325-336) were synthesized with optimal codon usage for expression in *E. coli* (Geneart, Regensburg, Germany) and subsequently cloned on the expression vector pET21 (Novagen, Madison, Wis.) using the restriction enzymes NdeI and XhoI. The three resulting expression plasmids pET21-Pdc1, pET21-Aro10 and pET21-KdcA, respectively, which also encoded a carboxy-terminal Hise-tag for each of the enzymes, were verified by DNA sequencing of the cloned structural genes (Eurofins Genomics, Ebersberg, Germany).

After chemical transformation of *E. coli* BL21 cells (Studier and Moffatt (1986) J. Mol. Biol. 189, 113-130) according to the $CaCl_2$-method (Sambrook et al. (1989) Molecular Cloning: A Laboratory Manual. Cold Spring Harbor Laboratory Press) with these expression plasmids, the enzymes Pdc1, Aro10 and KdcA were individually produced under control of the T7 promoter (Studier and Moffatt, ibid.). To this end, transformed bacteria were grown in 2 liter cultures in LB medium supplemented with 100 µg/ml ampicillin at 30° C. upon shaking until an $OD_{550}$ of 0.3-0.4 was reached. After lowering of the temperature during 45-60 min to 22° C., recombinant gene expression was induced at $OD_{550}$=0.6-0.8 for 5 h at 22° C. by addition of 0.01 mM isopropyl β-D-1-thiogalactopyranoside (IPTG). Finally, the bacteria were harvested by centrifugation (10 min, 6000 rpm, 4° C.) and the cell paste was frozen at −20° C.

All decarboxylases were purified using a two-step strategy comprising an immobilized metal ion affinity chromatography (IMAC) followed by a size exclusion chromatography (SEC). Therefore, the cells were resuspended in 3 ml 300 mM NaCl, 1 mM $MgSO_4$, 0.1 mM thiamine pyrophosphate (ThDP), 20 mM PIPES/NaOH pH 7.0 per 1 g wet weight and then disrupted mechanically using a French pressure cell (SLM Aminco, Rochester, N.Y.). The homogenate was centrifuged (30 min, 18000 rpm, 4° C.), and the complete supernatant was applied to a 5 ml bed volume HisTrap HP column (GE Healthcare, Munich, Germany) charged with Ni(II) ions using 300 mM NaCl, 1 mM $MgSO_4$, 0.1 mM ThDP, 20 mM PIPES/NaOH pH 7.0 as running buffer. The bound decarboxylase was eluted by a linear concentration gradient of 0 to 500 mM imidazole/HCl in running buffer. Main fractions containing the decarboxylase were identified by Commassie-stained SDS-PAGE and concentrated to a final volume of 2-2.5 ml using a centrifugal filter unit with a nominal molecular weight limit (NMWL) of 30 kDa (Merck, Darmstadt, Germany). The concentrated sample was further purified via SEC using a 120 ml bed volume HiLoad Superdex 200 16/60 column (GE Healthcare) in the presence of 500 mM NaCl, 1 mM MgSO$_4$, 0.5 mM ThDP, 20 mM PIPES/NaOH pH 7.0.

As result, all three decarboxylases were obtained with >90% purity as confirmed by Commassie-stained SDS-PAGE analysis. The yield was approximately 50 mg, 10 mg and 30 mg per 1 liter culture volume for Pdc1, Aro10 and KdcA, respectively.

Example 2: Production of Aminotransferases in *E. coli*

The gene for a methionine aminotransferase (YbdL) from *E. coli* (SEQ ID NO: 7; P77806; Dolzan et al. (2004) FEBS Lett. 571, 141-146) was amplified from *E. coli* K12 MG1655 using suitable primers and cloned on the expression vector pASK-IBA35(+) (IBA, Göttingen, Germany) using the restriction enzymes KasI and HindIII. The resulting expression plasmid pASK-IBA35(+)–YbdL, also encoding an amino-terminal His$_6$-tag for YbdL, was verified by DNA sequencing of the cloned structural gene (Eurofins Genomics).

The gene for an aromatic aminotransferase (Aro8) from *Saccharomyces cervisiae* (SEQ ID NO: 9; P53090; Bulfer et al. (2013) Protein Sci. 22, 1417-1424) was synthesized with optimal codon usage for expression in *E. coli* (Geneart) and cloned on the expression vector pASK-IBA35(+) using the restriction enzymes KasI and HindIII. The resulting expression plasmid pASK-IBA35(+)–Aro8, also encoding an amino-terminal Hise-tag for Aro8, was verified by DNA sequencing of the cloned structural gene (Eurofins Genomics).

Both enzymes, YbdL and Aro8, were produced in *E. coli* BL21 under control of the tet promoter (Skerra (1994) Gene 151, 131-135). Therefore, *E. coli* BL21 cells were transformed according to the CaCl$_2$-method (Sambrook et al., ibid.) with the corresponding expression plasmid and subsequently grown in 2 liter LB medium supplemented with 100 µg/ml ampicillin at 30° C. upon shaking until an OD$_{550}$=0.3-0.4 was reached. Then, the temperature was reduced to 22° C. during 45-60 min and recombinant gene expression was induced with 0.2 mg/l anhydrotetracycline (aTc; Acros, Geel, Belgium). After 5 h at 22° C. the bacteria were harvested by centrifugation (10 min, 6000 rpm, 4° C.) and frozen at −20° C.

To purify the aminotransferases, the cells containing each recombinant protein were resuspended in 3 ml 500 mM NaCl, 40 mM Tris/HCl pH 7.4 per 1 g wet weight. Then, the bacteria were disrupted mechanically in a French pressure cell. The homogenate was centrifuged (30 min, 18000 rpm, 4° C.) and the entire supernatant was applied to a 5 ml bed volume HisTrap HP column (GE Healthcare) charged with Ni(II) ions using 500 mM NaCl, 40 mM Tris/HCl pH 7.4 as running buffer. The bound aminotransferase was eluted by a linear concentration gradient of 0 to 500 mM imidazole/HCl in running buffer. Main fractions containing the aminotransferase were identified by Coomassie-stained SDS-PAGE and concentrated to a final volume of 4-5 ml using a centrifugal filter unit with a NMWL of 30 kDa. In a second step, the concentrated sample was purified by SEC using a 320 ml bed volume HiLoad Superdex 200 26/60 column in the presence of 500 mM NaCl, 20 mM Tris/HCl pH 7.4.

Both aminotransferases were obtained with >90% purity as confirmed by SDS-PAGE analysis with a yield of 18 mg/l for YbdL and 47 mg/l for Aro8.

Example 3: Production of Amino Acid Dehydrogenases in *E. coli*

The gene for the leucine dehydrogenase from *Bacillus sphaericus* (LeuDH; SEQ ID NO: 11; Li et al. (2009) Appl. Biochem. Biotechnol. 158, 343-351) and the gene for the Phenylalanine dehydrogenase from *Thermoactinomyces intermedius* (PheDH; SEQ ID NO: 13; P22823; Takada et al. (1991) J. Biochem. 109, 371-376) were synthesized with optimal codon usage for expression in *E. coli* (Geneart) and cloned on the expression vector pASK-IBA35(+) using the restriction enzymes KasI and HindIII. The resulting expression plasmids pASK-IBA35(+)–LeuDH and pASK-IBA35 (+)–PheDH, respectively, both also encoding an amino-terminal Hise-tag, were verified by DNA sequencing of the cloned structural gene (Eurofins Genomics).

LeuDH as well as PheDH were produced in *E. coli* BL21 under the same conditions as the aminotransferases described herein above in Example 2 with the exception that the culture was incubated for 5 h at 30° C. (instead of 22° C.) after induction with aTc.

For purification of both amino acid dehydrogenases the bacterial paste was resuspended in 3 ml 100 mM NaCl, 50 mM Tris/HCl pH 8.0 per 1 g wet cell mass and disrupted mechanically using a French pressure cell. After centrifugation (30 min, 18000 rpm, 4° C.), the supernatant was applied to a 5 ml bed volume HisTrap HP column (GE Healthcare) charged with Ni(II) ions using 100 mM NaCl, 50 mM Tris/HCl pH 8.0 as running buffer. The bound amino acid dehydrogenase was eluted by a linear concentration gradient of 0 to 500 mM imidazole/HCl in running buffer. Main fractions containing the amino acid dehydrogenase were identified by Coomassie-stained SDS-PAGE and concentrated to a final volume of 4-5 ml using a centrifugal filter unit with a NMWL of 30 kDa (Merck). In a second step, the concentrated sample was purified by SEC using a 320 ml bed volume HiLoad Superdex 200 26/60 column in the presence of 300 mM NaCl, 20 mM Tris/HCl pH 8.0.

The LeuDH and PheDH were obtained in yields of 7.5 mg/l and 19 mg/l, respectively. High purity of >95% was confirmed by Commassie-stained SDS-PAGE analysis.

Example 4: Synthesis of L-Methionine from 3-(Methylthio)Propanal (Methional) by a Two-Step Biocatalytic Reaction Involving a Decarboxylase and an Aminotransferase To synthesize L-methionine in a two-step biocatalytic reaction (FIG. 1A), the purified decarboxylase KdcA and the aminotransferase YbdL were mixed with the following reagents in a 10 ml pressure reactor (Tinyclave steel; Büchi, Uster, Switzerland) to a final volume of 1 ml:

| Reagent/enzyme | Final concentration |
| --- | --- |
| NaHCO$_3$ | 200 mM |
| ThDP | 0.5 mM |
| MgSO$_4$ | 1 mM |
| KdcA | 5 µM |
| YbdL | 5 µM |
| L-Glutamine | 50 mM |
| Methional | 4 mM |

The reaction was started by the addition of the substrate methional and application of 2 bar (200 kPa) CO$_2$. The initial pH of the mixture was 8, which shifted to ca. 6.5 upon application of CO$_2$ (as measured with a fixed-color pH indicator stick; Carl Roth, Karlsruhe, Germany). After 1 h incubation the mixture was collected from the reactor and centrifuged for 5 min at 13400 rpm in a bench top centrifuge to remove precipitated protein. Using the clear supernatant, product formation was analyzed by HPLC using a C18 column (Gemini C18, 4.6×15 mm, 3 μm, 110 Å; Phenomenex, Aschaffenburg, Germany) with isocratic elution in 4% (v/v) aqueous acetonitrile supplemented with 1% (v/v) phosphoric acid.

Figure 2A:
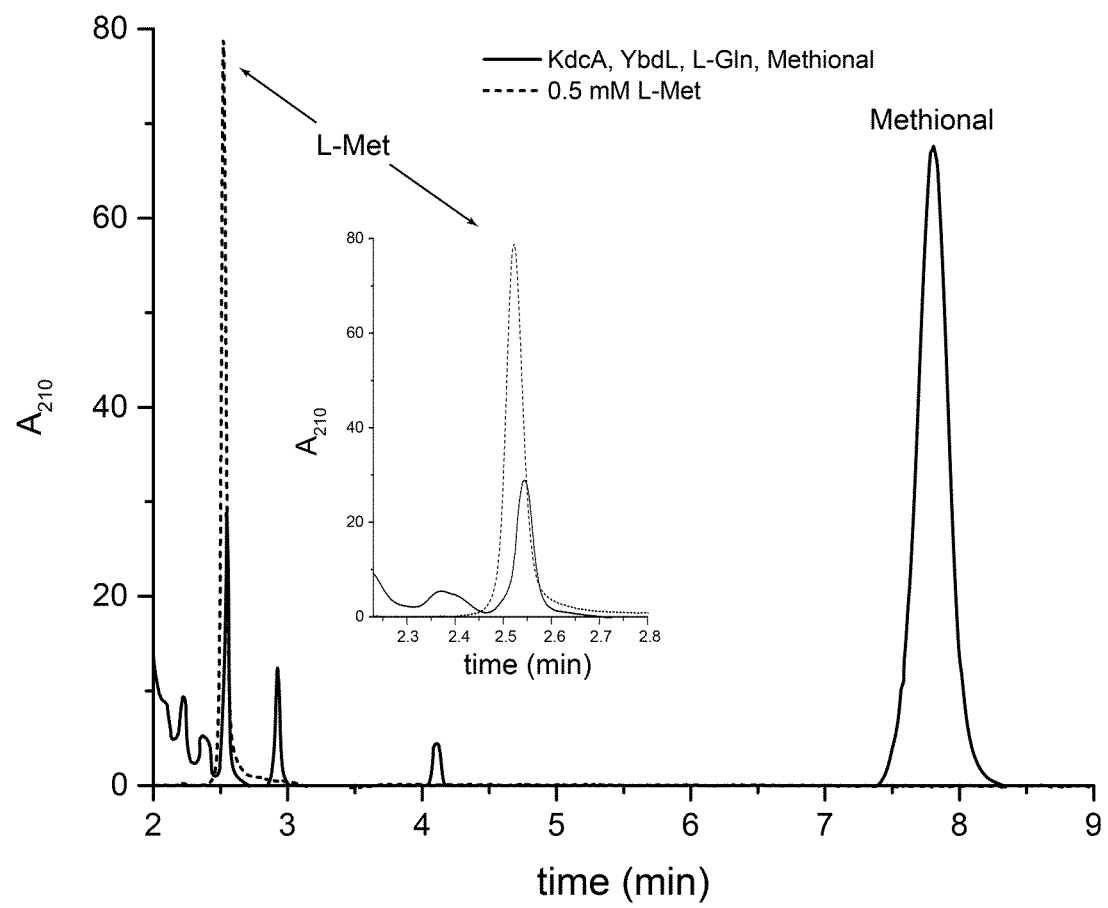
FIG. 2A: Detection of the reaction product L-methionine using HPLC analytics. The production of L-methionine was verified in a 5 µL sample from Example 4 via HPLC analytics using a C18 column (Gemini C18, 4.6×15 mm, 3 µm, 110 Å) and isocratic elution in 4% (v/v) aqueous acetonitrile supplemented with 1% v/v phosphoric acid. Methional and L-methionine were detected according to their absorption at 210 nm. L-Methionine synthesis for 105 min under 2 bar (200 kPa) $CO_2$ in the presence of 5 µM KdcA, 5 µM YbdL, 4 mM methional, 50 mM L-glutamine. The dotted trace corresponds to an L-methionine standard with defined concentration. Slight variations in the retention time correspond to the typical experimental error between repeated chromatography runs.
Figure 2B:
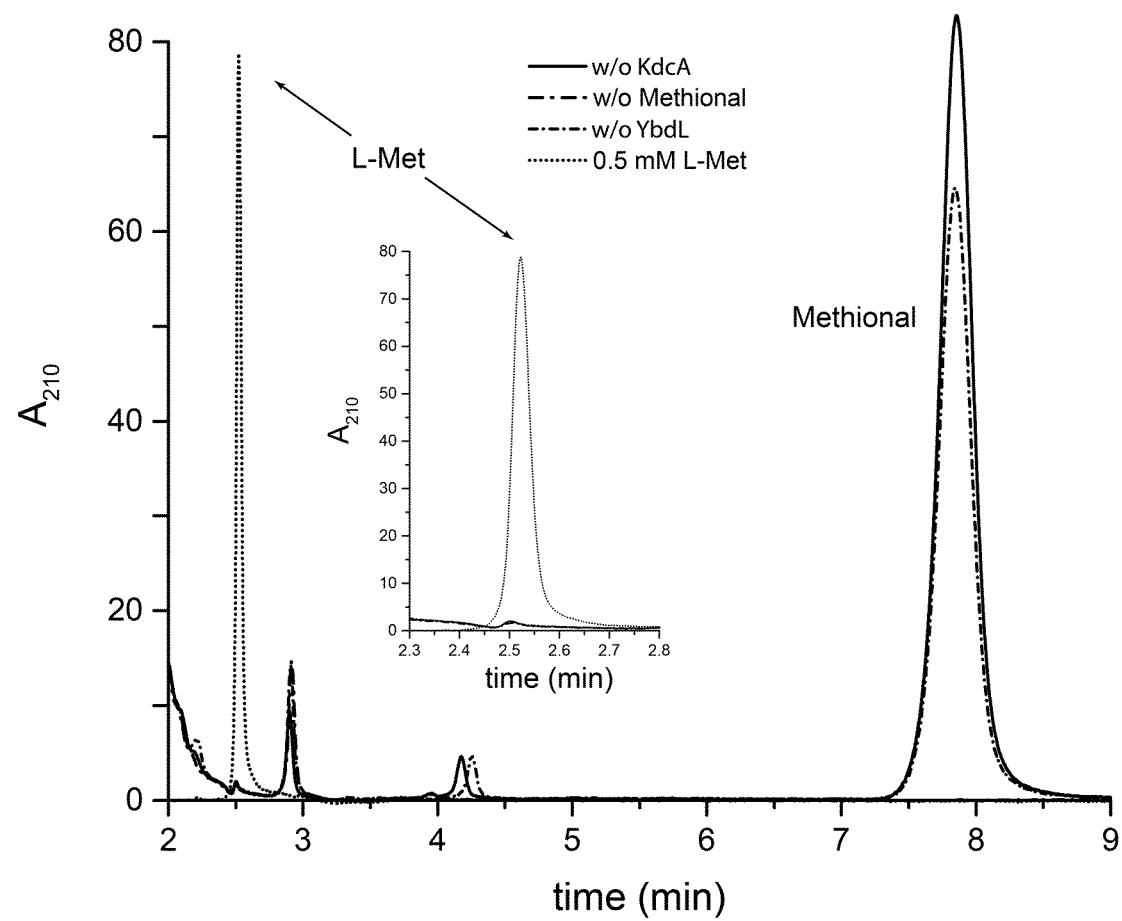
FIG. 2B: Control reactions under the same conditions as in (a) but omitting KdcA, YbdL or methional, respectively.
Figure 2C:
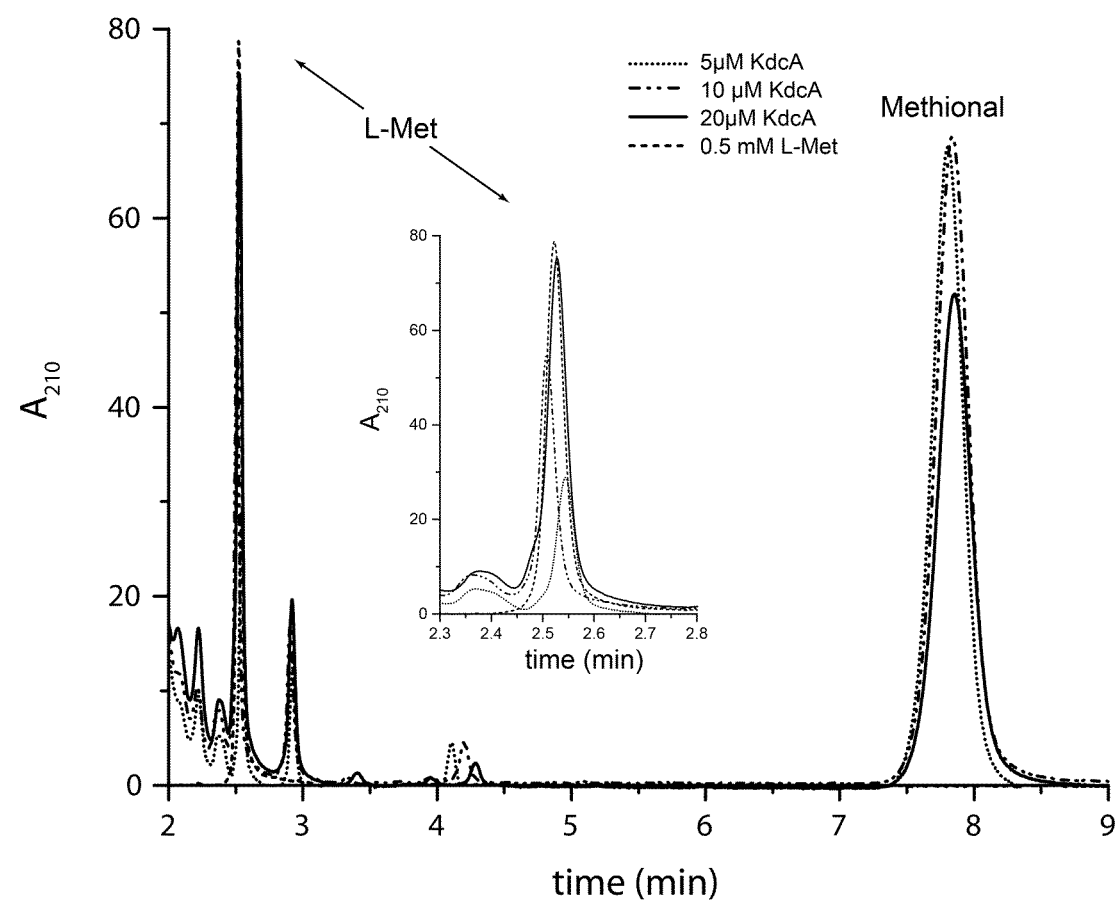
FIG. 2C: Increase of the L-methionine yield from 3%, as shown in (a), to 12.5% after optimization of reaction conditions using rising KdcA concentration: 5 or 10 or 20 µM KdcA, 5 µM YbdL, 4 mM methional, 50 mM L-glutamine; reaction for 105 min under 2 bar (200 kPa) $CO_2$.

Compared to control reactions with omission of KdcA, YbdL or methional, respectively (FIG. 2B), the chromatograms of the two-step biocatalytic synthesis in the presence of the decarboxylase (e.g. KdcA) and the aminotransferase (e.g. YbdL) as well as a donor amino acid (e.g. L-glutamine) clearly demonstrated that L-methionine was produced from methional (FIG. 2A). By increasing the concentration of the decarboxylase to 20 μM, the L-methionine yield was improved from 3% to 12.5% (FIG. 2C).

Figure 1B:
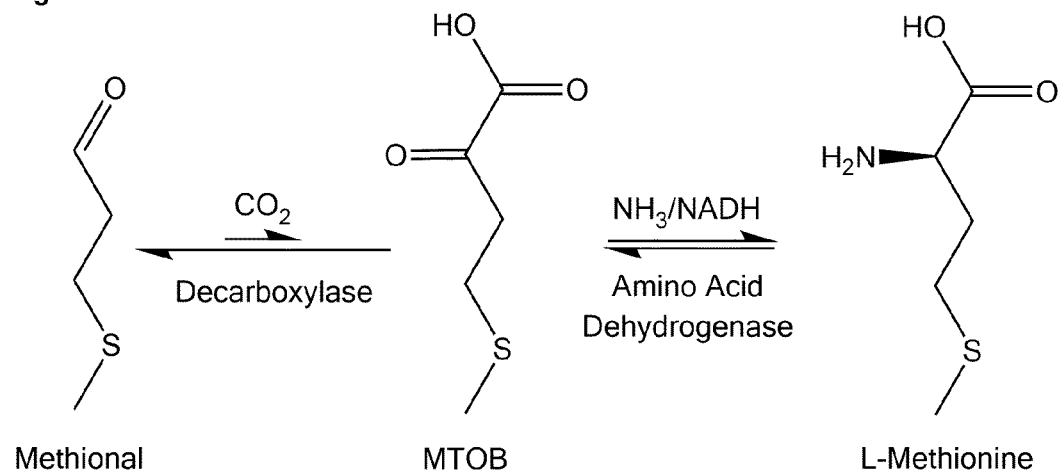
FIG. 1B: Scheme for the two-step biocatalytic synthesis of L-methionine from 3-(methylthio)propanal (methional) involving a decarboxylase and an amino acid dehydrogenase.
Figure 1C:
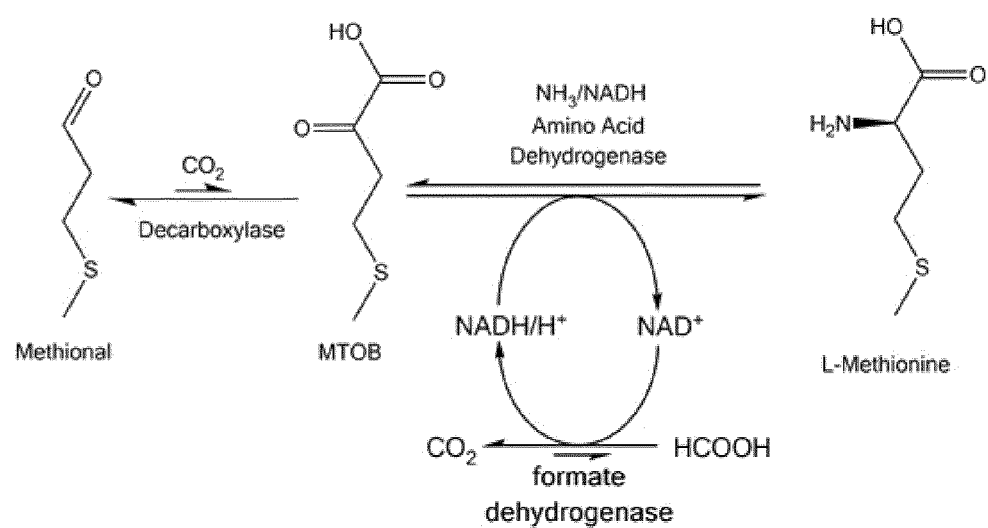
FIG. 1C: Scheme for the two-step biocatalytic synthesis of L-methionine from 3-(methylthio)propanal (methional) in the presence of a biocatalytic NADH regeneration system.

Example 5: Synthesis of L-Methionine from Methional by a Two-Step Biocatalytic Reaction Involving a Decarboxylase and an Amino Acid Dehydrogenase To synthesize L-methionine in a two-step biocatalytic reaction without the need for an amino donor cosubstrate (FIG. 1B), the purified decarboxylase KdcA and the amino acid dehydrogenase LeuDH were mixed with the following reagents in a 10 ml pressure reactor (Tinyclave steel) to a final volume of 1 ml:

| Reagent/enzyme | Final concentration |
|---|---|
| $NH_4HCO_3$ | 500 mM |
| ThDP | 0.5 mM |
| $MgSO_4$ | 1 mM |
| KdcA | 10 μM |
| LeuDH | 5 μM |
| NADH | 4 mM |
| Methional | 4 mM |

Like in Example 4, the reaction was started by the addition of methional and application of 2 bar (200 kPa) $CO_2$. The initial pH of the mixture was 8 and shifted to ca. 7 upon application of $CO_2$ (as measured with a fixed-color pH indicator stick). After 45 min incubation the mixture was recovered from the reactor and analyzed using HPLC as described in Example 4.

Figure 3A:
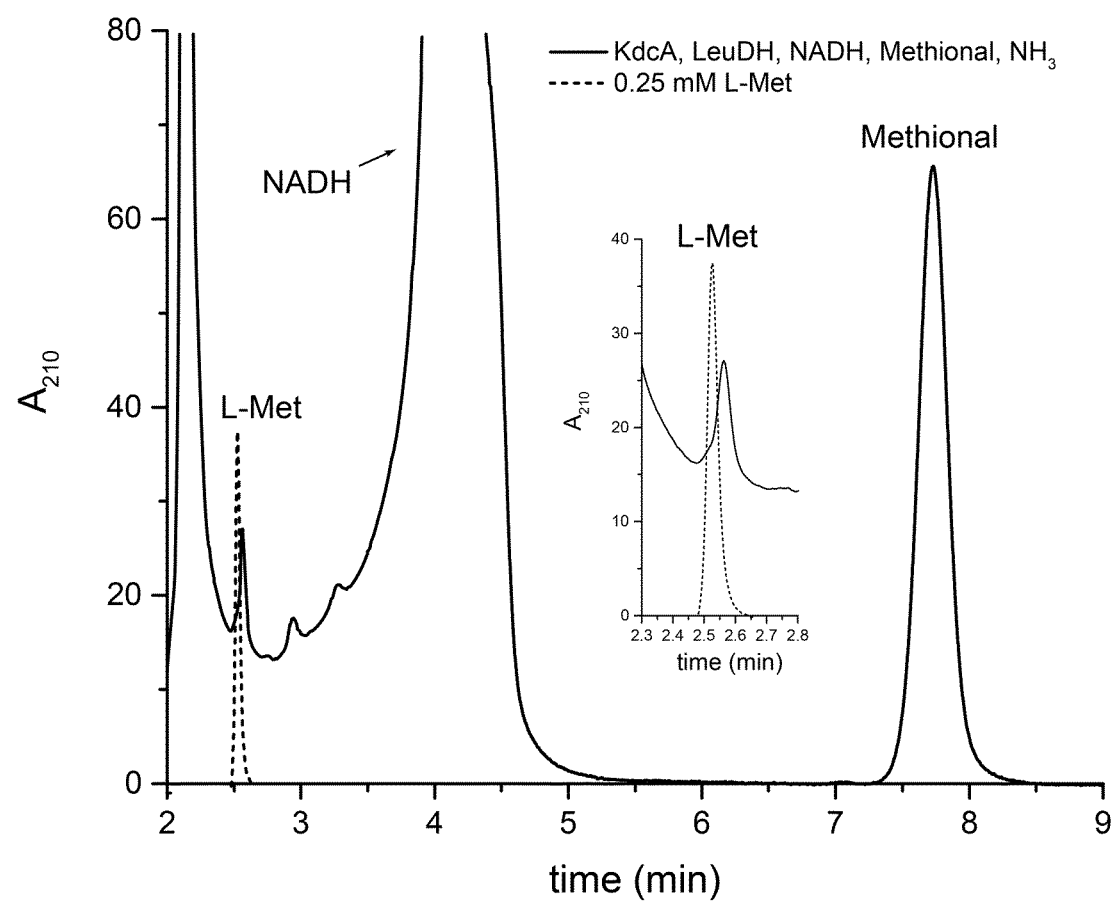
FIG. 3A: Detection of the reaction product L-methionine using HPLC analytics. The production of L-methionine was verified in a 5 µL sample from Example 5 via HPLC analytics using a C18 column (Gemini C18, 4.6×15 mm, 3 µm, 110 Å) and isocratic elution in 4% (v/v) aqueous acetonitrile supplemented with 1% v/v phosphoric acid. Methional and L-methionine were detected according to their absorption at 210 nm. L-Methionine synthesis for 45 min under 2 bar (200 kPa) $CO_2$ in the presence of 10 µM KdcA, 5 µM LeuDH, 4 mM methional, 4 mM NADH.
Figure 3B:
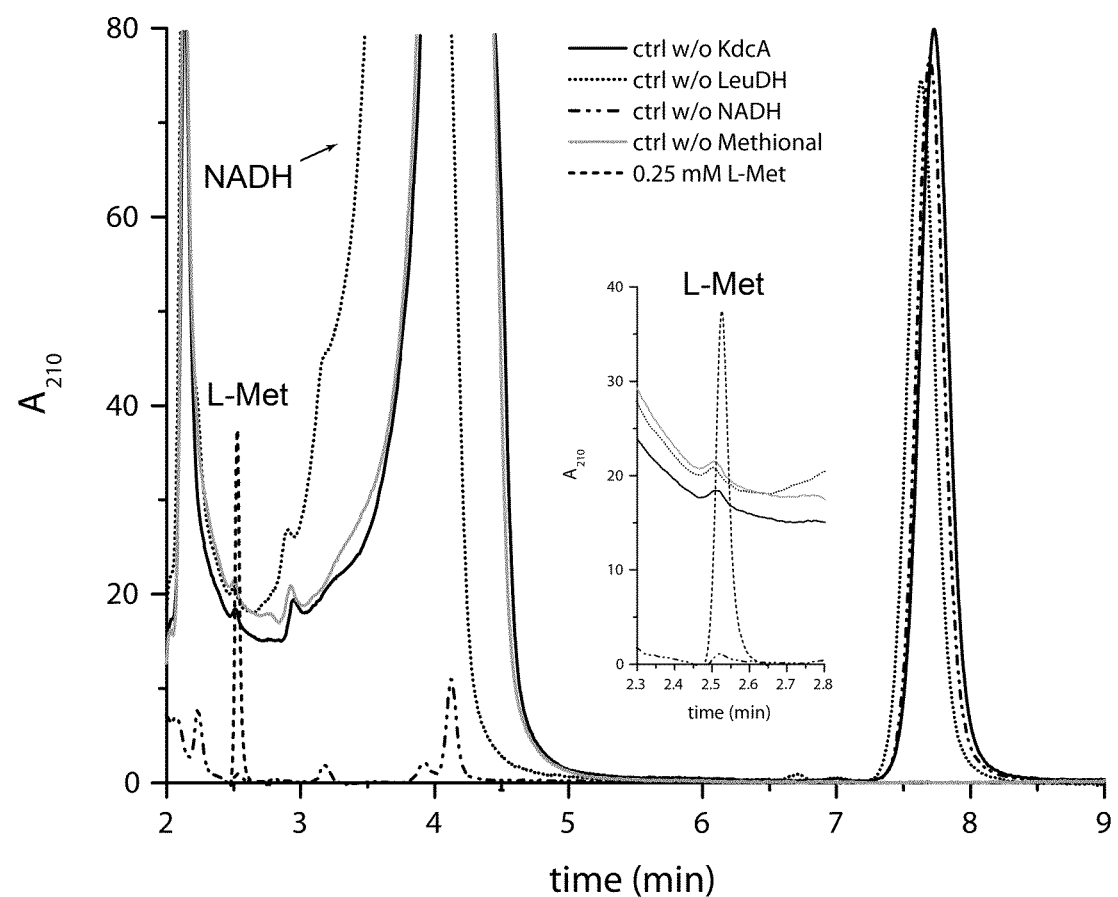
FIG. 3B: Control reactions under the same conditions as in (a) but omitting KdcA, LeuDH, methional or NADH, respectively.
Figure 3C:
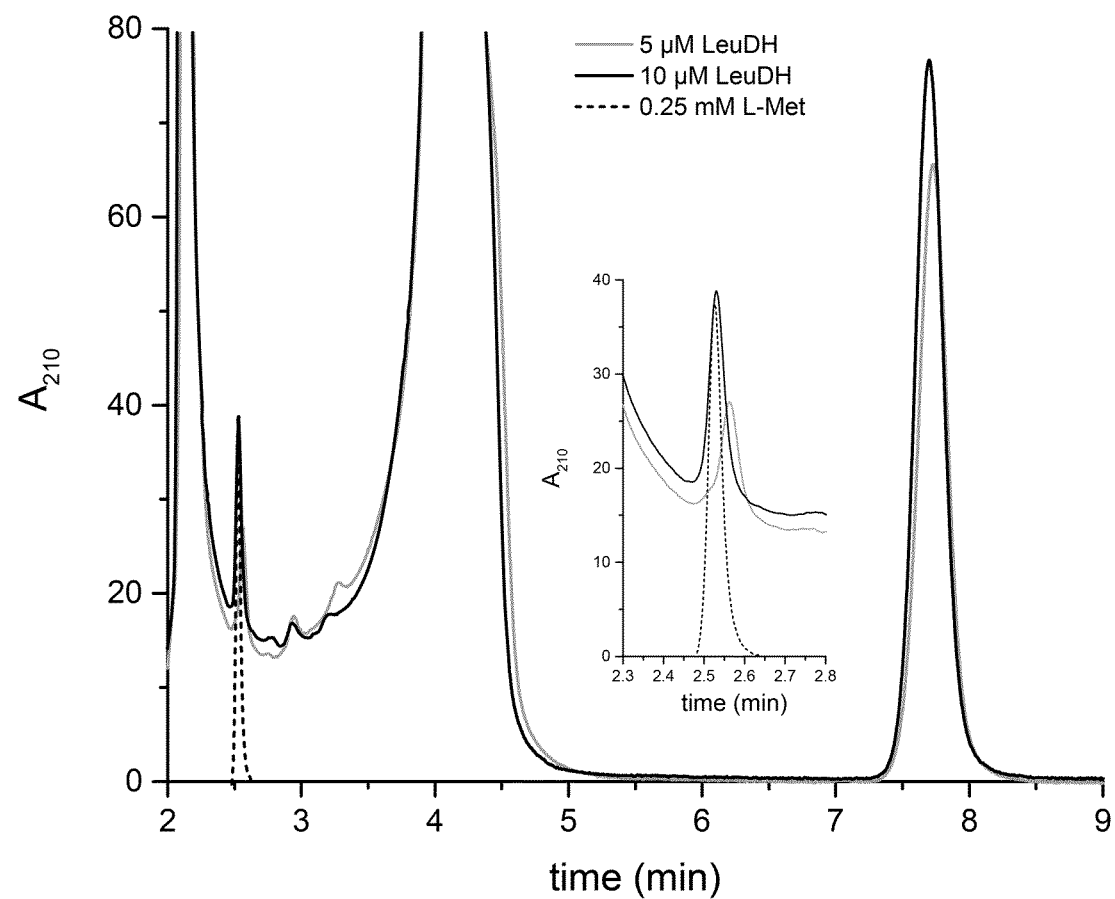
FIG. 3C: Increase of the L-methionine yield from 1.5%, as shown in (a), to 3% using doubled LeuDH concentration; reaction for 45 min under 2 bar (200 kPa) $CO_2$.

Compared to a control reaction with omission of the decarboxylase (e.g. KdcA), the amino acid dehydrogenase (e.g. LeuDH) or of NADH, respectively (FIG. 3B), the chromatograms of the two-step biocatalytic synthesis in the presence of a decarboxylase (e.g. KdcA) and an amino acid dehydrogenase (e.g. LeuDH) as well as NADH and an ammonium salt clearly demonstrated that L-methionine was produced from methional (FIG. 3A). By doubling the concentration of the amino acid dehydrogenase to 10 μM, the L-methionine yield was improved from 1.5% to 3% (FIG. 3C).

The invention claimed is:

1. A method for producing an L-amino acid, comprising: reacting a mixture comprising an aldehyde, carbon dioxide, a decarboxylase, a corresponding decarboxylase cofactor, and
   (a) at least one donor amino acid and an aminotransferase, and/or
   (b) NADH, ammonia and/or an ammonium salt and an amino acid dehydrogenase,
   thereby producing said L-amino acid or a salt thereof,
   wherein the L-amino acid produced is L-methionine and the aldehyde is 3-(methylthio)-propanal (methional),
   wherein the decarboxylase is at least one member selected from the group consisting of pyruvate decarboxylase PDC1, which originates from *Saccharomyces cerevisiae*, phenylpyruvate decarboxylase ARO10, which originates from *Saccharomyces cerevisiae*, and branched chain decarboxylase KdcA, which originates from *Lactococcus lactis*,
   wherein the aminotransferase, if present, is at least one member selected from the group consisting of methionine aminotransferase YbdL, which originates from *E. coli*, and aromatic aminotransferase Aro8, which originates from *Saccharomyces cerevisiae*, and
   wherein the amino acid dehydrogenase, if present, is at least one member selected from the group consisting of leucine dehydrogenase (LeuDH), which originates from *Bacillus sphaericus*, and phenylalanine dehydrogenase (PheDH), which originates from *Thermoactinomyces intermedius*.

2. The method as claimed in claim 1, wherein the corresponding decarboxylase cofactor comprises thiamine pyrophosphate.

3. The method as claimed in claim 1, wherein the donor amino acid is present, is different from the L-amino acid produced, and is at least one L-amino acid selected from the group consisting of L-glutamine, L-glutamate, L-alanine, L-phenylalanine, L-tyrosine, L-leucine, L-isoleucine, L-histidine and L-tryptophan.

4. The method as claimed in claim 1, wherein the carbon dioxide is applied to the mixture at a pressure from 10 to 7400 kPa.

5. The method as claimed in claim 1, wherein the mixture further comprises formic acid or a salt thereof and a formate dehydrogenase.

6. The method as claimed in claim 5, wherein the formate dehydrogenase is at least one member selected from the group consisting of formate dehydrogenase from *Pseudomonas* sp. and formate dehydrogenase from *Candida* sp. as well as mutants and variants of these formate dehydrogenases having formate dehydrogenase activity.

\* \* \* \* \*

SEQUENCE LISTING

```
<160> NUMBER OF SEQ ID NOS: 14

<210> SEQ ID NO 1
<211> LENGTH: 1719
<212> TYPE: DNA
<213> ORGANISM: Saccharomyces cerevisiae
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(1719)
<223> OTHER INFORMATION: sequence of PDC1 of Sacharomyces cerevisiae
      optimized for the codon usage of Escherichia coli with a carboxy-
      terminal His6-tag
<220> FEATURE:
<221> NAME/KEY: misc_feature
<222> LOCATION: (1693)..(1698)
<223> OTHER INFORMATION: XhoI restriction site

<400> SEQUENCE: 1 cat atg agc gaa att acc ctg ggc aaa tac ctg ttt gaa cgc ctg aaa        48
    Met Ser Glu Ile Thr Leu Gly Lys Tyr Leu Phe Glu Arg Leu Lys
    1               5                  10                  15 cag gtt aat gtg aat acc gtt ttt ggt ctg cct ggc gat ttt aat ctg        96
Gln Val Asn Val Asn Thr Val Phe Gly Leu Pro Gly Asp Phe Asn Leu
                20                  25                  30 agc ctg ctg gat aaa atc tat gaa gtt gaa ggt atg cgt tgg gca ggt       144
Ser Leu Leu Asp Lys Ile Tyr Glu Val Glu Gly Met Arg Trp Ala Gly
            35                  40                  45 aat gca aat gaa ctg aat gca gcc tat gca gca gat ggt tat gca cgt       192
Asn Ala Asn Glu Leu Asn Ala Ala Tyr Ala Ala Asp Gly Tyr Ala Arg
        50                  55                  60 att aaa ggt atg agc tgc att att acc acc ttt ggt gtt ggt gaa ctg       240
```

-continued

| | | | | | | | | | | | | | | | |
|---|---|---|---|---|---|---|---|---|---|---|---|---|---|---|---|
|Ile|Lys|Gly|Met|Ser|Cys|Ile|Ile|Thr|Thr|Phe|Gly|Val|Gly|Glu|Leu|
| |65| | | |70| | | | |75| | | | | |

```
agc gca ctg aat ggt att gca ggt agc tat gca gaa cat gtt ggt gtg    288
Ser Ala Leu Asn Gly Ile Ala Gly Ser Tyr Ala Glu His Val Gly Val
 80              85                  90                  95 ctg cat gtt gtt ggt gtt ccg agc att agc gca cag gca aaa cag ctg    336
Leu His Val Val Gly Val Pro Ser Ile Ser Ala Gln Ala Lys Gln Leu
                100                 105                 110 ctg ctg cat cat acc ctg ggt aat ggt gat ttt acc gtg ttt cat cgt    384
Leu Leu His His Thr Leu Gly Asn Gly Asp Phe Thr Val Phe His Arg
            115                 120                 125 atg agc gca aat att agc gaa acc acc gca atg att acc gat att gca    432
Met Ser Ala Asn Ile Ser Glu Thr Thr Ala Met Ile Thr Asp Ile Ala
        130                 135                 140 acc gca ccg gca gaa att gat cgt tgt att cgt acc acc tat gtt acc    480
Thr Ala Pro Ala Glu Ile Asp Arg Cys Ile Arg Thr Thr Tyr Val Thr
    145                 150                 155 cag cgt ccg gtt tat ctg ggt ctg cca gca aat ctg gtt gat ctg aat    528
Gln Arg Pro Val Tyr Leu Gly Leu Pro Ala Asn Leu Val Asp Leu Asn
160                 165                 170                 175 gtt ccg gct aaa ctg ctg caa acc ccg att gat atg agc ctg aaa ccg    576
Val Pro Ala Lys Leu Leu Gln Thr Pro Ile Asp Met Ser Leu Lys Pro
                180                 185                 190 aat gat gca gaa agc gaa aaa gaa gtg att gat acc att ctg gcc ctg    624
Asn Asp Ala Glu Ser Glu Lys Glu Val Ile Asp Thr Ile Leu Ala Leu
            195                 200                 205 gtt aaa gat gca aaa aat ccg gtt att ctg gca gat gcc tgt tgt agc    672
Val Lys Asp Ala Lys Asn Pro Val Ile Leu Ala Asp Ala Cys Cys Ser
        210                 215                 220 cgt cat gat gtt aaa gca gaa acc aaa aaa ctg atc gac ctg acc cag    720
Arg His Asp Val Lys Ala Glu Thr Lys Lys Leu Ile Asp Leu Thr Gln
    225                 230                 235 ttt ccg gca ttt gtt acc ccg atg ggt aaa ggt agc att gat gaa cag    768
Phe Pro Ala Phe Val Thr Pro Met Gly Lys Gly Ser Ile Asp Glu Gln
240                 245                 250                 255 cat ccg cgt tat ggt ggt gtt tat gtt ggc acc ctg agc aaa ccg gaa    816
His Pro Arg Tyr Gly Gly Val Tyr Val Gly Thr Leu Ser Lys Pro Glu
                260                 265                 270 gtt aaa gaa gca gtt gaa agc gca gat ctg att ctg agc gtt ggt gca    864
Val Lys Glu Ala Val Glu Ser Ala Asp Leu Ile Leu Ser Val Gly Ala
            275                 280                 285 ctg ctg agt gat ttt aac acc ggt agc ttt tcg tat agc tac aaa acg    912
Leu Leu Ser Asp Phe Asn Thr Gly Ser Phe Ser Tyr Ser Tyr Lys Thr
        290                 295                 300 aaa aac atc gtc gag ttt cat agc gat cac atg aaa att cgt aat gca    960
Lys Asn Ile Val Glu Phe His Ser Asp His Met Lys Ile Arg Asn Ala
    305                 310                 315 acc ttt ccg ggt gtg cag atg aaa ttt gtt ctg caa aaa ctg ctg acc   1008
Thr Phe Pro Gly Val Gln Met Lys Phe Val Leu Gln Lys Leu Leu Thr
320                 325                 330                 335 acc att gca gat gca gca aaa ggt tat aaa ccg gtt gca gtt ccg gca   1056
Thr Ile Ala Asp Ala Ala Lys Gly Tyr Lys Pro Val Ala Val Pro Ala
                340                 345                 350 cgt aca ccg gca aat gca gcc gtt ccg gca tca aca ccg ctg aaa caa   1104
Arg Thr Pro Ala Asn Ala Ala Val Pro Ala Ser Thr Pro Leu Lys Gln
            355                 360                 365 gaa tgg atg tgg aat cag ctg ggt aat ttt ctg caa gag ggt gat gtt   1152
Glu Trp Met Trp Asn Gln Leu Gly Asn Phe Leu Gln Glu Gly Asp Val
        370                 375                 380
```

| | | | | | | | | | | | | | | | | |
|---|---|---|---|---|---|---|---|---|---|---|---|---|---|---|---|---|
| gtt | att | gca | gaa | acc | ggc | acc | agc | gca | ttt | ggt | att | aat | cag | acc | acc | 1200 |
| Val | Ile | Ala | Glu | Thr | Gly | Thr | Ser | Ala | Phe | Gly | Ile | Asn | Gln | Thr | Thr | |
| | 385 | | | | 390 | | | | | 395 | | | | | | |
| ttt | ccg | aat | aac | acc | tat | ggt | att | agc | cag | gtt | ctg | tgg | ggt | agt | att | 1248 |
| Phe | Pro | Asn | Asn | Thr | Tyr | Gly | Ile | Ser | Gln | Val | Leu | Trp | Gly | Ser | Ile | |
| 400 | | | | | 405 | | | | | 410 | | | | | 415 | |
| ggt | ttt | acc | acc | ggt | gca | acc | ctg | ggt | gca | gca | ttt | gca | gcc | gaa | gaa | 1296 |
| Gly | Phe | Thr | Thr | Gly | Ala | Thr | Leu | Gly | Ala | Ala | Phe | Ala | Ala | Glu | Glu | |
| | | | | 420 | | | | | 425 | | | | | 430 | | |
| atc | gat | ccg | aaa | aaa | cgt | gtg | att | ctg | ttt | att | ggt | gat | ggt | agc | ctg | 1344 |
| Ile | Asp | Pro | Lys | Lys | Arg | Val | Ile | Leu | Phe | Ile | Gly | Asp | Gly | Ser | Leu | |
| | | | 435 | | | | | 440 | | | | | 445 | | | |
| caa | ctg | acc | gtt | caa | gaa | att | agc | acc | atg | att | cgt | tgg | ggt | ctg | aaa | 1392 |
| Gln | Leu | Thr | Val | Gln | Glu | Ile | Ser | Thr | Met | Ile | Arg | Trp | Gly | Leu | Lys | |
| | | 450 | | | | | 455 | | | | | 460 | | | | |
| ccg | tac | ctg | ttc | gtt | ctg | aat | aat | gat | ggc | tat | acc | atc | gag | aaa | ctg | 1440 |
| Pro | Tyr | Leu | Phe | Val | Leu | Asn | Asn | Asp | Gly | Tyr | Thr | Ile | Glu | Lys | Leu | |
| | 465 | | | | | 470 | | | | | 475 | | | | | |
| atc | cac | ggt | ccg | aaa | gca | cag | tat | aat | gaa | att | cag | ggt | tgg | gat | cat | 1488 |
| Ile | His | Gly | Pro | Lys | Ala | Gln | Tyr | Asn | Glu | Ile | Gln | Gly | Trp | Asp | His | |
| 480 | | | | | 485 | | | | | 490 | | | | | 495 | |
| ctg | tca | ctg | ctg | ccg | acc | ttt | ggc | gca | aaa | gat | tat | gaa | aca | cat | cgt | 1536 |
| Leu | Ser | Leu | Leu | Pro | Thr | Phe | Gly | Ala | Lys | Asp | Tyr | Glu | Thr | His | Arg | |
| | | | | 500 | | | | | 505 | | | | | 510 | | |
| gtt | gca | acc | aca | ggt | gaa | tgg | gat | aaa | ctg | acc | cag | gat | aaa | tcc | ttt | 1584 |
| Val | Ala | Thr | Thr | Gly | Glu | Trp | Asp | Lys | Leu | Thr | Gln | Asp | Lys | Ser | Phe | |
| | | | 515 | | | | | 520 | | | | | 525 | | | |
| aat | gat | aac | agc | aaa | atc | cgc | atg | atc | gaa | att | atg | ctg | ccg | gtt | ttt | 1632 |
| Asn | Asp | Asn | Ser | Lys | Ile | Arg | Met | Ile | Glu | Ile | Met | Leu | Pro | Val | Phe | |
| | | 530 | | | | | 535 | | | | | 540 | | | | |
| gat | gca | ccg | cag | aat | ctg | gtg | gaa | cag | gcc | aaa | ctg | acc | gca | gca | acc | 1680 |
| Asp | Ala | Pro | Gln | Asn | Leu | Val | Glu | Gln | Ala | Lys | Leu | Thr | Ala | Ala | Thr | |
| | 545 | | | | | 550 | | | | | 555 | | | | | |
| aat | gca | aaa | cag | ctc | gag | cac | cac | cac | cac | cac | cac | tga | | | | 1719 |
| Asn | Ala | Lys | Gln | Leu | Glu | His | His | His | His | His | His | | | | | |
| 560 | | | | | 565 | | | | | 570 | | | | | | |

```
<210> SEQ ID NO 2
<211> LENGTH: 571
<212> TYPE: PRT
<213> ORGANISM: Saccharomyces cerevisiae

<400> SEQUENCE: 2
```

| | | | | | | | | | | | | | | |
|---|---|---|---|---|---|---|---|---|---|---|---|---|---|---|
| Met | Ser | Glu | Ile | Thr | Leu | Gly | Lys | Tyr | Leu | Phe | Glu | Arg | Leu | Lys | Gln |
| 1 | | | | 5 | | | | | 10 | | | | | 15 | |
| Val | Asn | Val | Asn | Thr | Val | Phe | Gly | Leu | Pro | Gly | Asp | Phe | Asn | Leu | Ser |
| | | | 20 | | | | | 25 | | | | | 30 | | |
| Leu | Leu | Asp | Lys | Ile | Tyr | Glu | Val | Glu | Gly | Met | Arg | Trp | Ala | Gly | Asn |
| | | 35 | | | | | 40 | | | | | 45 | | | |
| Ala | Asn | Glu | Leu | Asn | Ala | Ala | Tyr | Ala | Ala | Asp | Gly | Tyr | Ala | Arg | Ile |
| | 50 | | | | | 55 | | | | | 60 | | | | |
| Lys | Gly | Met | Ser | Cys | Ile | Ile | Thr | Thr | Phe | Gly | Val | Gly | Glu | Leu | Ser |
| 65 | | | | 70 | | | | | 75 | | | | | 80 | |
| Ala | Leu | Asn | Gly | Ile | Ala | Gly | Ser | Tyr | Ala | Glu | His | Val | Gly | Val | Leu |
| | | | 85 | | | | | 90 | | | | | 95 | | |
| His | Val | Val | Gly | Val | Pro | Ser | Ile | Ser | Ala | Gln | Ala | Lys | Gln | Leu | Leu |
| | | | 100 | | | | | 105 | | | | | 110 | | |
| Leu | His | His | Thr | Leu | Gly | Asn | Gly | Asp | Phe | Thr | Val | Phe | His | Arg | Met |
| | | 115 | | | | | 120 | | | | | 125 | | | |

```
Ser Ala Asn Ile Ser Glu Thr Thr Ala Met Ile Thr Asp Ile Ala Thr
        130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
                180                 185                 190

Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
530                 535                 540
```

```
Ala Pro Gln Asn Leu Val Glu Gln Ala Lys Leu Thr Ala Ala Thr Asn
545                 550                 555                 560

Ala Lys Gln Leu Glu His His His His His His
                565                 570
```

<210> SEQ ID NO 3
<211> LENGTH: 1932
<212> TYPE: DNA
<213> ORGANISM: Saccharomyces cerevisiae
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(1932)
<223> OTHER INFORMATION: sequence of ARO10 of Sacharomyces cerevisiae
    optimized for the codon usage of Escherichia coli with a carboxy-
    terminal His6-tag
<220> FEATURE:
<221> NAME/KEY: misc_feature
<222> LOCATION: (1906)..(1911)
<223> OTHER INFORMATION: XhoI restriction site

<400> SEQUENCE: 3

```
cat atg gca ccg gtt acc att gaa aaa ttc gtg aat caa gaa gaa cgc      48
    Met Ala Pro Val Thr Ile Glu Lys Phe Val Asn Gln Glu Glu Arg
    1               5                   10                  15 cac ctg gtt agc aat cgt agc gca acc att ccg ttt ggt gaa tat atc     96
His Leu Val Ser Asn Arg Ser Ala Thr Ile Pro Phe Gly Glu Tyr Ile
                20                  25                  30 ttt aaa cgc ctg ctg agc att gat acc aaa agc gtg ttt ggt gtt ccg    144
Phe Lys Arg Leu Leu Ser Ile Asp Thr Lys Ser Val Phe Gly Val Pro
            35                  40                  45 ggt gat ttt aat ctg agc ctg ctg gaa tat ctg tat agc ccg agc gtt    192
Gly Asp Phe Asn Leu Ser Leu Leu Glu Tyr Leu Tyr Ser Pro Ser Val
        50                  55                  60 gaa agc gca ggt ctg cgt tgg gtt ggc acc tgt aat gaa ctg aat gca    240
Glu Ser Ala Gly Leu Arg Trp Val Gly Thr Cys Asn Glu Leu Asn Ala
65                  70                  75 gcc tat gca gca gat ggt tat agc cgt tat agc aac aaa att ggt tgt    288
Ala Tyr Ala Ala Asp Gly Tyr Ser Arg Tyr Ser Asn Lys Ile Gly Cys
80                  85                  90                  95 ctg att acc acc tat ggt gtt ggt gaa ctg agc gca ctg aat ggt att    336
Leu Ile Thr Thr Tyr Gly Val Gly Glu Leu Ser Ala Leu Asn Gly Ile
                100                 105                 110 gca ggt agc ttt gca gaa aat gtg aaa gtg ctg cat att gtt ggt gtg    384
Ala Gly Ser Phe Ala Glu Asn Val Lys Val Leu His Ile Val Gly Val
            115                 120                 125 gcc aaa agt att gat agc cgt agc agc aat ttt agc gat cgt aat ctg    432
Ala Lys Ser Ile Asp Ser Arg Ser Ser Asn Phe Ser Asp Arg Asn Leu
        130                 135                 140 cat cat ctg gtt ccg cag ctg cat gat agc aac ttt aaa ggt ccg aac    480
His His Leu Val Pro Gln Leu His Asp Ser Asn Phe Lys Gly Pro Asn
145                 150                 155 cat aaa gtg tat cac gac atg gtt aaa gat cgt gtt gca tgt agc gtt    528
His Lys Val Tyr His Asp Met Val Lys Asp Arg Val Ala Cys Ser Val
160                 165                 170                 175 gca tat ctg gaa gat att gaa acc gca tgt gat cag gtg gat aat gtg    576
Ala Tyr Leu Glu Asp Ile Glu Thr Ala Cys Asp Gln Val Asp Asn Val
                180                 185                 190 att cgc gat atc tat aaa tac agc aaa ccg ggt tat atc ttt gtg cct    624
Ile Arg Asp Ile Tyr Lys Tyr Ser Lys Pro Gly Tyr Ile Phe Val Pro
            195                 200                 205
```

-continued

| | |
|---|---|
| gcc gat ttt gca gat atg agc gtt acc tgt gat aat ctg gtt aat gtt<br>Ala Asp Phe Ala Asp Met Ser Val Thr Cys Asp Asn Leu Val Asn Val<br>210                         215                    220 | 672 |
| ccg cgt att agc cag cag gat tgt att gtt tat ccg agc gaa aat cag<br>Pro Arg Ile Ser Gln Gln Asp Cys Ile Val Tyr Pro Ser Glu Asn Gln<br>225                      230                    235 | 720 |
| ctg agc gac att att aac aaa atc acc agc tgg atc tat agc agc aaa<br>Leu Ser Asp Ile Ile Asn Lys Ile Thr Ser Trp Ile Tyr Ser Ser Lys<br>240                         245                    250                    255 | 768 |
| aca ccg gca att ctg ggt gat gtt ctg acc gat cgt tat ggt gtt agc<br>Thr Pro Ala Ile Leu Gly Asp Val Leu Thr Asp Arg Tyr Gly Val Ser<br>                    260                    265                    270 | 816 |
| aat ttt ctg aac aaa ctg att tgc aaa acc ggc atc tgg aat ttt tct<br>Asn Phe Leu Asn Lys Leu Ile Cys Lys Thr Gly Ile Trp Asn Phe Ser<br>               275                    280                    285 | 864 |
| acc gtt atg ggt aaa agc gtg atc gat gaa agc aat ccg acc tat atg<br>Thr Val Met Gly Lys Ser Val Ile Asp Glu Ser Asn Pro Thr Tyr Met<br>290                         295                    300 | 912 |
| ggt cag tat aat ggt aaa gaa ggc ctg aaa cag gtc tat gaa cat ttt<br>Gly Gln Tyr Asn Gly Lys Glu Gly Leu Lys Gln Val Tyr Glu His Phe<br>305                         310                    315 | 960 |
| gaa ctg tgt gat ctg gtg ctg cat ttt ggc gtt gac att aac gaa att<br>Glu Leu Cys Asp Leu Val Leu His Phe Gly Val Asp Ile Asn Glu Ile<br>320                       325                    330                    335 | 1008 |
| aac aac ggc cat tac acc ttc acc tat aaa ccg aat gca aaa atc atc<br>Asn Asn Gly His Tyr Thr Phe Thr Tyr Lys Pro Asn Ala Lys Ile Ile<br>               340                    345                    350 | 1056 |
| cag ttc cac ccg aac tat att cgt ctg gtt gat acc cgt cag ggt aat<br>Gln Phe His Pro Asn Tyr Ile Arg Leu Val Asp Thr Arg Gln Gly Asn<br>               355                    360                    365 | 1104 |
| gag cag atg ttt aaa ggt att aac ttt gca ccg atc ctg aaa gag ctg<br>Glu Gln Met Phe Lys Gly Ile Asn Phe Ala Pro Ile Leu Lys Glu Leu<br>             370                    375                    380 | 1152 |
| tat aaa cgt att gat gtg agc aaa ctg tcc ctg caa tat gat agt aat<br>Tyr Lys Arg Ile Asp Val Ser Lys Leu Ser Leu Gln Tyr Asp Ser Asn<br>385                         390                    395 | 1200 |
| gtt acc cag tat acc aac gaa acc atg cgc ctg gaa gat ccg acc aat<br>Val Thr Gln Tyr Thr Asn Glu Thr Met Arg Leu Glu Asp Pro Thr Asn<br>400                         405                    410                    415 | 1248 |
| ggt cag agc agc att att acc cag gtt cat ctg caa aaa acg atg ccg<br>Gly Gln Ser Ser Ile Ile Thr Gln Val His Leu Gln Lys Thr Met Pro<br>               420                    425                    430 | 1296 |
| aaa ttt ctg aat cca ggt gat gtt gtt gtt tgt gaa acc ggt agc ttt<br>Lys Phe Leu Asn Pro Gly Asp Val Val Val Cys Glu Thr Gly Ser Phe<br>               435                    440                    445 | 1344 |
| cag ttt agc gtt cgt gat ttt gca ttt ccg agc cag ctg aaa tat atc<br>Gln Phe Ser Val Arg Asp Phe Ala Phe Pro Ser Gln Leu Lys Tyr Ile<br>             450                    455                    460 | 1392 |
| agc cag ggt ttt ttt ctg agt att ggt atg gca ctg cct gcc gca ctg<br>Ser Gln Gly Phe Phe Leu Ser Ile Gly Met Ala Leu Pro Ala Ala Leu<br>465                         470                    475 | 1440 |
| ggt gtt ggt atc gca atg cag gat cat agc aat gca cat att aat ggt<br>Gly Val Gly Ile Ala Met Gln Asp His Ser Asn Ala His Ile Asn Gly<br>480                         485                    490                    495 | 1488 |
| ggc aac gtg aaa gag gat tat aaa ccg cgt ctg att ctg ttt gaa ggt<br>Gly Asn Val Lys Glu Asp Tyr Lys Pro Arg Leu Ile Leu Phe Glu Gly<br>               500                    505                    510 | 1536 |
| gat ggt gca gca cag atg acc att caa gaa ctg agc acc att ctg aaa<br>Asp Gly Ala Ala Gln Met Thr Ile Gln Glu Leu Ser Thr Ile Leu Lys | 1584 |

| | | | | | | | | | | | | | | | | |
|---|---|---|---|---|---|---|---|---|---|---|---|---|---|---|---|---|
| | | 515 | | | | 520 | | | | | 525 | | | | | |
| tgt | aat | att | ccg | ctg | gaa | gtg | atc | atc | tgg | aac | aat | aat | ggt | tat | acg | 1632 |
| Cys | Asn | Ile | Pro | Leu | Glu | Val | Ile | Ile | Trp | Asn | Asn | Asn | Gly | Tyr | Thr | |
| | | 530 | | | | 535 | | | | 540 | | | | | | |
| att | gag | cgt | gca | att | atg | ggt | ccg | acc | cgt | agc | tat | aat | gat | gtt | atg | 1680 |
| Ile | Glu | Arg | Ala | Ile | Met | Gly | Pro | Thr | Arg | Ser | Tyr | Asn | Asp | Val | Met | |
| 545 | | | | | 550 | | | | | 555 | | | | | | |
| agc | tgg | aaa | tgg | acc | aaa | ctg | ttt | gag | gca | ttt | ggc | gat | ttt | gat | ggc | 1728 |
| Ser | Trp | Lys | Trp | Thr | Lys | Leu | Phe | Glu | Ala | Phe | Gly | Asp | Phe | Asp | Gly | |
| 560 | | | | 565 | | | | | 570 | | | | | 575 | | |
| aaa | tat | acc | aat | agc | acc | ctg | att | cag | tgt | ccg | agt | aaa | ctg | gca | ctg | 1776 |
| Lys | Tyr | Thr | Asn | Ser | Thr | Leu | Ile | Gln | Cys | Pro | Ser | Lys | Leu | Ala | Leu | |
| | | | 580 | | | | | 585 | | | | | 590 | | | |
| aaa | ctg | gaa | gaa | ctg | aaa | aac | agc | aat | aaa | cgc | agc | ggt | att | gaa | ctg | 1824 |
| Lys | Leu | Glu | Glu | Leu | Lys | Asn | Ser | Asn | Lys | Arg | Ser | Gly | Ile | Glu | Leu | |
| | | 595 | | | | | 600 | | | | | 605 | | | | |
| ctg | gaa | gtt | aaa | ctg | ggc | gaa | ctg | gat | ttt | ccg | gaa | caa | ctg | aaa | tgc | 1872 |
| Leu | Glu | Val | Lys | Leu | Gly | Glu | Leu | Asp | Phe | Pro | Glu | Gln | Leu | Lys | Cys | |
| | | | 610 | | | | | 615 | | | | | 620 | | | |
| atg | gtt | gaa | gca | gca | gcc | ctg | aaa | cgt | aat | aaa | ctc | gag | cac | cac | cac | 1920 |
| Met | Val | Glu | Ala | Ala | Ala | Leu | Lys | Arg | Asn | Lys | Leu | Glu | His | His | His | |
| | 625 | | | | | 630 | | | | | 635 | | | | | |
| cac | cac | cac | tga | | | | | | | | | | | | | 1932 |
| His | His | His | | | | | | | | | | | | | | |
| 640 | | | | | | | | | | | | | | | | |

<210> SEQ ID NO 4
<211> LENGTH: 642
<212> TYPE: PRT
<213> ORGANISM: Saccharomyces cerevisiae

<400> SEQUENCE: 4

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Asn Phe Ser Asp Arg Asn Leu His
    130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala

```
            195                 200                 205
Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
            245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
            275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
            325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
            355                 360                 365

Gln Met Phe Lys Gly Ile Asn Phe Ala Pro Ile Leu Lys Glu Leu Tyr
370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
            405                 410                 415

Gln Ser Ser Ile Ile Thr Gln Val His Leu Gln Lys Thr Met Pro Lys
            420                 425                 430

Phe Leu Asn Pro Gly Asp Val Val Val Cys Glu Thr Gly Ser Phe Gln
            435                 440                 445

Phe Ser Val Arg Asp Phe Ala Phe Pro Ser Gln Leu Lys Tyr Ile Ser
450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
            485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
            565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
            595                 600                 605

Glu Val Lys Leu Gly Glu Leu Asp Phe Pro Glu Gln Leu Lys Cys Met
            610                 615                 620
```

```
Val Glu Ala Ala Ala Leu Lys Arg Asn Lys Leu Glu His His His His
625                 630                 635                 640

His His
```

```
<210> SEQ ID NO 5
<211> LENGTH: 1671
<212> TYPE: DNA
<213> ORGANISM: Lactococcus lactis
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(1671)
<223> OTHER INFORMATION: sequence of kdcA of Lactococcus lactis
      optimized for the codon usage of Escherichia coli with a carboxy-
      terminal His6-tag
<220> FEATURE:
<221> NAME/KEY: misc_feature
<222> LOCATION: (1645)..(1650)
<223> OTHER INFORMATION: XhoI restriction site

<400> SEQUENCE: 5
```

```
cat atg tat acc gtt ggt gat tat ctg ctg gat cgt ctg cat gaa ctg        48
    Met Tyr Thr Val Gly Asp Tyr Leu Leu Asp Arg Leu His Glu Leu
    1               5                  10                  15 ggt att gaa gaa att ttt ggt gtt ccg ggt gat tac aac ctg caa ttt        96
Gly Ile Glu Glu Ile Phe Gly Val Pro Gly Asp Tyr Asn Leu Gln Phe
            20                  25                  30 ctg gat cag att atc agc cgt gaa gat atg aaa tgg att ggc aat gcg       144
Leu Asp Gln Ile Ile Ser Arg Glu Asp Met Lys Trp Ile Gly Asn Ala
        35                  40                  45 aat gaa ctg aat gca agc tat atg gca gat ggt tat gca cgt acc aaa       192
Asn Glu Leu Asn Ala Ser Tyr Met Ala Asp Gly Tyr Ala Arg Thr Lys
    50                  55                  60 aaa gca gca gca ttt ctg acc acc ttt ggt gtt ggt gaa ctg agc gca       240
Lys Ala Ala Ala Phe Leu Thr Thr Phe Gly Val Gly Glu Leu Ser Ala
65                  70                  75 att aat ggt ctg gca ggt agc tat gca gaa aat ctg ccg gtt gtt gaa       288
Ile Asn Gly Leu Ala Gly Ser Tyr Ala Glu Asn Leu Pro Val Val Glu
80                  85                  90                  95 att gtt ggt agc ccg acc agc aaa gtt cag aat gat ggt aaa ttt gtg       336
Ile Val Gly Ser Pro Thr Ser Lys Val Gln Asn Asp Gly Lys Phe Val
            100                 105                 110 cat cat acc ctg gcc gat ggt gat ttt aaa cac ttt atg aaa atg cac       384
His His Thr Leu Ala Asp Gly Asp Phe Lys His Phe Met Lys Met His
        115                 120                 125 gaa ccg gtt acc gca gca cgt acc ctg ctg acc gca gaa aat gca acc       432
Glu Pro Val Thr Ala Ala Arg Thr Leu Leu Thr Ala Glu Asn Ala Thr
    130                 135                 140 tat gaa att gat cgt gtt ctg agc cag ctg ctg aaa gaa cgt aaa ccg       480
Tyr Glu Ile Asp Arg Val Leu Ser Gln Leu Leu Lys Glu Arg Lys Pro
145                 150                 155 gtg tat att aac ctg ccg gtt gat gtt gca gca gca aaa gca gaa aaa       528
Val Tyr Ile Asn Leu Pro Val Asp Val Ala Ala Ala Lys Ala Glu Lys
160                 165                 170                 175 ccg gca ctg agc ctg gaa aaa gaa agc agc acc acc aat acc acc gaa       576
Pro Ala Leu Ser Leu Glu Lys Glu Ser Ser Thr Thr Asn Thr Thr Glu
            180                 185                 190 cag gtt att ctg agc aaa atc gaa gaa agc ctg aaa aat gcc cag aaa       624
Gln Val Ile Leu Ser Lys Ile Glu Glu Ser Leu Lys Asn Ala Gln Lys
        195                 200                 205
```

```
                                                              -continued ccg gtt gtt att gca ggt cat gaa gtt att agc ttt ggg ctg gaa aaa      672
Pro Val Val Ile Ala Gly His Glu Val Ile Ser Phe Gly Leu Glu Lys
        210                 215                 220 acc gtt acc cag ttt gtt agc gaa acc aaa ctg ccg att acc acc ctg      720
Thr Val Thr Gln Phe Val Ser Glu Thr Lys Leu Pro Ile Thr Thr Leu
    225                 230                 235 aat ttt ggt aaa agc gca gtt gat gaa agc ctg ccg agc ttt ctg ggt      768
Asn Phe Gly Lys Ser Ala Val Asp Glu Ser Leu Pro Ser Phe Leu Gly
240                 245                 250                 255 atc tat aat ggt aaa ctg tcc gag atc tcc ctg aaa aac ttt gtt gaa      816
Ile Tyr Asn Gly Lys Leu Ser Glu Ile Ser Leu Lys Asn Phe Val Glu
                260                 265                 270 agc gca gat ttc att ctg atg ctg ggt gtt aaa ctg acc gat agc agt      864
Ser Ala Asp Phe Ile Leu Met Leu Gly Val Lys Leu Thr Asp Ser Ser
            275                 280                 285 acc ggt gca ttt acc cat cat ctg gat gaa aac aaa atg atc agc ctg      912
Thr Gly Ala Phe Thr His His Leu Asp Glu Asn Lys Met Ile Ser Leu
        290                 295                 300 aac att gat gag ggc atc atc ttt aac aaa gtg gtg gaa gat ttt gat      960
Asn Ile Asp Glu Gly Ile Ile Phe Asn Lys Val Val Glu Asp Phe Asp
305                 310                 315 ttt cgt gca gtt gtt agc agc ctg agc gaa ctg aaa ggt att gaa tat     1008
Phe Arg Ala Val Val Ser Ser Leu Ser Glu Leu Lys Gly Ile Glu Tyr
320                 325                 330                 335 gaa ggc cag tac atc gac aaa cag tat gaa gaa ttt att ccg agc agc     1056
Glu Gly Gln Tyr Ile Asp Lys Gln Tyr Glu Glu Phe Ile Pro Ser Ser
                340                 345                 350 gca ccg ctg agc cag gat cgc ctg tgg cag gca gtt gaa agt ctg acc     1104
Ala Pro Leu Ser Gln Asp Arg Leu Trp Gln Ala Val Glu Ser Leu Thr
            355                 360                 365 cag agc aat gaa acc att gtt gca gaa cag ggc acc agt ttt ttt ggt     1152
Gln Ser Asn Glu Thr Ile Val Ala Glu Gln Gly Thr Ser Phe Phe Gly
        370                 375                 380 gca agc acc att ttt ctg aaa agc aac agc cgt ttt att ggt cag ccg     1200
Ala Ser Thr Ile Phe Leu Lys Ser Asn Ser Arg Phe Ile Gly Gln Pro
385                 390                 395 ctg tgg ggt agc att ggt tat acc ttt ccg gca gca ctg ggt agc cag     1248
Leu Trp Gly Ser Ile Gly Tyr Thr Phe Pro Ala Ala Leu Gly Ser Gln
400                 405                 410                 415 att gca gat aaa gaa agc cgt cat ctg ctg ttt att ggt gat ggt agc     1296
Ile Ala Asp Lys Glu Ser Arg His Leu Leu Phe Ile Gly Asp Gly Ser
                420                 425                 430 ctg caa ctg acc gtt caa gaa ctg ggt ctg agc att cgt gaa aaa ctg     1344
Leu Gln Leu Thr Val Gln Glu Leu Gly Leu Ser Ile Arg Glu Lys Leu
            435                 440                 445 aat ccg att tgc ttc atc att aac aac gat ggc tat acc gtg gaa cgt     1392
Asn Pro Ile Cys Phe Ile Ile Asn Asn Asp Gly Tyr Thr Val Glu Arg
        450                 455                 460 gaa att cat ggt ccg acc cag agt tat aat gat att ccg atg tgg aac     1440
Glu Ile His Gly Pro Thr Gln Ser Tyr Asn Asp Ile Pro Met Trp Asn
    465                 470                 475 tac tcg aaa ctg cct gaa acc ttt ggc gca acc gaa gat cgt gtg gtt     1488
Tyr Ser Lys Leu Pro Glu Thr Phe Gly Ala Thr Glu Asp Arg Val Val
480                 485                 490                 495 agc aaa att gtt cgt acc gaa aat gaa ttt gtg agc gtg atg aaa gaa     1536
Ser Lys Ile Val Arg Thr Glu Asn Glu Phe Val Ser Val Met Lys Glu
                500                 505                 510 gca cag gca gac gtt aat cgt atg tat tgg att gaa ctg gtg ctg gaa     1584
Ala Gln Ala Asp Val Asn Arg Met Tyr Trp Ile Glu Leu Val Leu Glu
```

```
                    515                 520                 525
aaa gag gat gca ccg aaa ctg ctg aaa aaa atg ggt aaa ctg ttt gcc    1632
Lys Glu Asp Ala Pro Lys Leu Leu Lys Lys Met Gly Lys Leu Phe Ala
            530                 535                 540 gag cag aat aaa ctc gag cac cac cac cac cac tga                    1671
Glu Gln Asn Lys Leu Glu His His His His His
        545                 550             555

<210> SEQ ID NO 6
<211> LENGTH: 555
<212> TYPE: PRT
<213> ORGANISM: Lactococcus lactis

<400> SEQUENCE: 6

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
```

```
                    325                 330                 335
Gly Gln Tyr Ile Asp Lys Gln Tyr Glu Glu Phe Ile Pro Ser Ser Ala
                340                 345                 350

Pro Leu Ser Gln Asp Arg Leu Trp Gln Ala Val Glu Ser Leu Thr Gln
            355                 360                 365

Ser Asn Glu Thr Ile Val Ala Glu Gln Gly Thr Ser Phe Phe Gly Ala
        370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
530                 535                 540

Gln Asn Lys Leu Glu His His His His His
545                 550                 555

<210> SEQ ID NO 7
<211> LENGTH: 1207
<212> TYPE: DNA
<213> ORGANISM: Escherichia coli
<220> FEATURE:
<221> NAME/KEY: CDS
<222> LOCATION: (1)..(1203)
<223> OTHER INFORMATION: sequence of ybdL of Escherichia coli with an
      amino-terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1202)..(1207)
<223> OTHER INFORMATION: HindIII restriction site

<400> SEQUENCE: 7 atg gct agc aga gga tcg cat cac cat cac cat cac ggc gcc atg aca      48
Met Ala Ser Arg Gly Ser His His His His His His Gly Ala Met Thr
1               5                   10                  15 aat aac cct ctg att cca caa agc aaa ctt cca caa ctt ggc acc act      96
Asn Asn Pro Leu Ile Pro Gln Ser Lys Leu Pro Gln Leu Gly Thr Thr
                20                  25                  30 att ttc acc cag atg agc gcg ctg gcg cag caa cac cag gcg att aac      144
Ile Phe Thr Gln Met Ser Ala Leu Ala Gln Gln His Gln Ala Ile Asn
            35                  40                  45 ctg tcg caa ggc ttt cct gat ttt gat ggt ccg cgc tat tta cag gag      192
Leu Ser Gln Gly Phe Pro Asp Phe Asp Gly Pro Arg Tyr Leu Gln Glu
```

```
            50                  55                  60
cgg ctg gcg cac cac gtt gca cag ggg gca aac caa tac gcg ccc atg    240
Arg Leu Ala His His Val Ala Gln Gly Ala Asn Gln Tyr Ala Pro Met
 65                  70                  75                  80 acc ggc gtg cag gcc ttg cgc gag gcg att gct cag aaa acg gaa cgt    288
Thr Gly Val Gln Ala Leu Arg Glu Ala Ile Ala Gln Lys Thr Glu Arg
                     85                  90                  95 ttg tat ggc tat caa cca gat gcc gat agc gat atc acc gta acg gca    336
Leu Tyr Gly Tyr Gln Pro Asp Ala Asp Ser Asp Ile Thr Val Thr Ala
                100                 105                 110 ggg gcg acg gaa gcg tta tac gcg gcg att acc gca ctg gtg cgc aat    384
Gly Ala Thr Glu Ala Leu Tyr Ala Ala Ile Thr Ala Leu Val Arg Asn
            115                 120                 125 ggc gat gaa gtg att tgt ttt gat ccc agc tat gac agt tac gcc ccc    432
Gly Asp Glu Val Ile Cys Phe Asp Pro Ser Tyr Asp Ser Tyr Ala Pro
130                 135                 140 gcc atc gcg ctt tct ggg gga ata gtg aag cgt atg gca ctg caa cca    480
Ala Ile Ala Leu Ser Gly Gly Ile Val Lys Arg Met Ala Leu Gln Pro
145                 150                 155                 160 ccg cat ttt cgc gtt gac tgg cag gaa ttt gcc gca tta tta agc gag    528
Pro His Phe Arg Val Asp Trp Gln Glu Phe Ala Ala Leu Leu Ser Glu
                165                 170                 175 cgc acc aga ctg gtg atc ctc aac act ccg cat aac ccc agt gca act    576
Arg Thr Arg Leu Val Ile Leu Asn Thr Pro His Asn Pro Ser Ala Thr
                180                 185                 190 gtc tgg cag cag gct gat ttc gcc gct ttg tgg cag gcg atc gcc ggg    624
Val Trp Gln Gln Ala Asp Phe Ala Ala Leu Trp Gln Ala Ile Ala Gly
            195                 200                 205 cac gag att ttt gtc att agc gat gaa gtc tac gag cac atc aac ttt    672
His Glu Ile Phe Val Ile Ser Asp Glu Val Tyr Glu His Ile Asn Phe
210                 215                 220 tca caa cag ggc cat gcc agt gtg ctg gcg cat ccg cag ctg cgt gag    720
Ser Gln Gln Gly His Ala Ser Val Leu Ala His Pro Gln Leu Arg Glu
225                 230                 235                 240 cgg gca gtg gcg gtt tct tca ttt ggc aag acc tat cat atg acc ggc    768
Arg Ala Val Ala Val Ser Ser Phe Gly Lys Thr Tyr His Met Thr Gly
                245                 250                 255 tgg aaa gtg ggt tat tgt gtt gcg cca gcg ccc atc agc gcc gaa att    816
Trp Lys Val Gly Tyr Cys Val Ala Pro Ala Pro Ile Ser Ala Glu Ile
                260                 265                 270 cgc aag gta cat cag tat ctg acc ttt tcg gtg aat acc ccg gca cag    864
Arg Lys Val His Gln Tyr Leu Thr Phe Ser Val Asn Thr Pro Ala Gln
            275                 280                 285 ctg gcg ctt gct gat atg cta cgt gca gaa cct gag cat tat ctt gcg    912
Leu Ala Leu Ala Asp Met Leu Arg Ala Glu Pro Glu His Tyr Leu Ala
290                 295                 300 tta ccg gac ttt tat cgc cag aag cgc gat att ctg gtg aat gct tta    960
Leu Pro Asp Phe Tyr Arg Gln Lys Arg Asp Ile Leu Val Asn Ala Leu
305                 310                 315                 320 aat gaa agc cgg ctg gag att tta ccg tgt gaa ggt aca tac ttt ttg   1008
Asn Glu Ser Arg Leu Glu Ile Leu Pro Cys Glu Gly Thr Tyr Phe Leu
                325                 330                 335 ctg gtg gat tac agc gcg gtt tct acc ctg gat gat gtt gag ttt tgc   1056
Leu Val Asp Tyr Ser Ala Val Ser Thr Leu Asp Asp Val Glu Phe Cys
                340                 345                 350 cag tgg ctg acg cag gag cac ggc gta gcg gcg att ccg ctg tcg gtg   1104
Gln Trp Leu Thr Gln Glu His Gly Val Ala Ala Ile Pro Leu Ser Val
            355                 360                 365 ttt tgc gcc gat ccc ttc cca cat aaa ctg att cgt ctc tgt ttt gcc   1152
```

```
Phe Cys Ala Asp Pro Phe Pro His Lys Leu Ile Arg Leu Cys Phe Ala
            370                 375                 380 aag aag gaa tcg acg ttg ctg gca gca gct gaa cgc ctg cgc cag ctt    1200
Lys Lys Glu Ser Thr Leu Leu Ala Ala Ala Glu Arg Leu Arg Gln Leu
385                 390                 395                 400 taa gctt                                                           1207

<210> SEQ ID NO 8
<211> LENGTH: 400
<212> TYPE: PRT
<213> ORGANISM: Escherichia coli

<400> SEQUENCE: 8

Met Ala Ser Arg Gly Ser His His His His His His Gly Ala Met Thr
1               5                   10                  15

Asn Asn Pro Leu Ile Pro Gln Ser Lys Leu Pro Gln Leu Gly Thr Thr
            20                  25                  30

Ile Phe Thr Gln Met Ser Ala Leu Ala Gln Gln His Gln Ala Ile Asn
        35                  40                  45

Leu Ser Gln Gly Phe Pro Asp Phe Asp Gly Pro Arg Tyr Leu Gln Glu
    50                  55                  60

Arg Leu Ala His His Val Ala Gln Gly Ala Asn Gln Tyr Ala Pro Met
65                  70                  75                  80

Thr Gly Val Gln Ala Leu Arg Glu Ala Ile Ala Gln Lys Thr Glu Arg
                85                  90                  95

Leu Tyr Gly Tyr Gln Pro Asp Ala Asp Ser Asp Ile Thr Val Thr Ala
            100                 105                 110

Gly Ala Thr Glu Ala Leu Tyr Ala Ala Ile Thr Ala Leu Val Arg Asn
        115                 120                 125

Gly Asp Glu Val Ile Cys Phe Asp Pro Ser Tyr Asp Ser Tyr Ala Pro
    130                 135                 140

Ala Ile Ala Leu Ser Gly Gly Ile Val Lys Arg Met Ala Leu Gln Pro
145                 150                 155                 160

Pro His Phe Arg Val Asp Trp Gln Glu Phe Ala Ala Leu Leu Ser Glu
                165                 170                 175

Arg Thr Arg Leu Val Ile Leu Asn Thr Pro His Asn Pro Ser Ala Thr
            180                 185                 190

Val Trp Gln Gln Ala Asp Phe Ala Ala Leu Trp Gln Ala Ile Ala Gly
        195                 200                 205

His Glu Ile Phe Val Ile Ser Asp Glu Val Tyr Glu His Ile Asn Phe
    210                 215                 220

Ser Gln Gln Gly His Ala Ser Val Leu Ala His Pro Gln Leu Arg Glu
225                 230                 235                 240

Arg Ala Val Ala Val Ser Ser Phe Gly Lys Thr Tyr His Met Thr Gly
                245                 250                 255

Trp Lys Val Gly Tyr Cys Val Ala Pro Ala Pro Ile Ser Ala Glu Ile
            260                 265                 270

Arg Lys Val His Gln Tyr Leu Thr Phe Ser Val Asn Thr Pro Ala Gln
        275                 280                 285

Leu Ala Leu Ala Asp Met Leu Arg Ala Glu Pro Glu His Tyr Leu Ala
    290                 295                 300

Leu Pro Asp Phe Tyr Arg Gln Lys Arg Asp Ile Leu Val Asn Ala Leu
305                 310                 315                 320

Asn Glu Ser Arg Leu Glu Ile Leu Pro Cys Glu Gly Thr Tyr Phe Leu
                325                 330                 335
```

```
Leu Val Asp Tyr Ser Ala Val Ser Thr Leu Asp Asp Val Glu Phe Cys
            340                 345                 350

Gln Trp Leu Thr Gln Glu His Gly Val Ala Ala Ile Pro Leu Ser Val
            355                 360                 365

Phe Cys Ala Asp Pro Phe Pro His Lys Leu Ile Arg Leu Cys Phe Ala
370                 375                 380

Lys Lys Glu Ser Thr Leu Leu Ala Ala Ala Glu Arg Leu Arg Gln Leu
385                 390                 395                 400

<210> SEQ ID NO 9
<211> LENGTH: 1549
<212> TYPE: DNA
<213> ORGANISM: Saccharomyces cerevisiae
<220> FEATURE:
<221> NAME/KEY: CDS
<222> LOCATION: (1)..(1545)
<223> OTHER INFORMATION: sequence of ARO8 of Saccharomyces cerevisiae
      optimized for the codon usage of Escherichia coli with an amino-
      terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1544)..(1549)
<223> OTHER INFORMATION: HindIII restriction site

<400> SEQUENCE: 9 atg gct agc aga gga tcg cat cac cat cac cat cac ggc gcc atg acc       48
Met Ala Ser Arg Gly Ser His His His His His His Gly Ala Met Thr
1               5                   10                  15 ctg ccg gaa agc aaa gat ttt agc tac ctg ttt tcc gat gaa acc aat       96
Leu Pro Glu Ser Lys Asp Phe Ser Tyr Leu Phe Ser Asp Glu Thr Asn
            20                  25                  30 gca cgt aaa ccg agt ccg ctg aaa acc tgt att cat tta ttt cag gat      144
Ala Arg Lys Pro Ser Pro Leu Lys Thr Cys Ile His Leu Phe Gln Asp
        35                  40                  45 ccg aac atc atc ttt ctg ggt ggt ggt ctg ccg ctg aaa gat tat ttt      192
Pro Asn Ile Ile Phe Leu Gly Gly Gly Leu Pro Leu Lys Asp Tyr Phe
    50                  55                  60 ccg tgg gat aat ctg agc gtt gat agc ccg aaa ccg cct ttt ccg cag      240
Pro Trp Asp Asn Leu Ser Val Asp Ser Pro Lys Pro Pro Phe Pro Gln
65                  70                  75                  80 ggt att ggt gca ccg att gat gaa cag aat tgc atc aaa tac acc gtg      288
Gly Ile Gly Ala Pro Ile Asp Glu Gln Asn Cys Ile Lys Tyr Thr Val
                85                  90                  95 aac aaa gat tac gca gat aaa agc gca aat ccg agc aat gat att ccg      336
Asn Lys Asp Tyr Ala Asp Lys Ser Ala Asn Pro Ser Asn Asp Ile Pro
            100                 105                 110 ctg agc cgt gca ctg cag tat ggt ttt agc gca ggt cag ccg gaa ctg      384
Leu Ser Arg Ala Leu Gln Tyr Gly Phe Ser Ala Gly Gln Pro Glu Leu
        115                 120                 125 ctg aac ttt att cgt gat cat acc aaa atc atc cac gat ctg aaa tac      432
Leu Asn Phe Ile Arg Asp His Thr Lys Ile Ile His Asp Leu Lys Tyr
    130                 135                 140 aaa gat tgg gat gtt ctg gca acc gca ggt aat acc aat gca tgg gaa      480
Lys Asp Trp Asp Val Leu Ala Thr Ala Gly Asn Thr Asn Ala Trp Glu
145                 150                 155                 160 agc acc ctg cgt gtt ttt tgt aat cgt ggt gat gtt att ctg gtt gaa      528
Ser Thr Leu Arg Val Phe Cys Asn Arg Gly Asp Val Ile Leu Val Glu
                165                 170                 175
```

```
gca cat agc ttt agc agc agc ctg gca agt gcc gaa gca cag ggt gtt        576
Ala His Ser Phe Ser Ser Ser Leu Ala Ser Ala Glu Ala Gln Gly Val
            180                 185                 190 att acc ttt ccg gtt ccg atc gat gca gat ggt att att ccg gaa aaa        624
Ile Thr Phe Pro Val Pro Ile Asp Ala Asp Gly Ile Ile Pro Glu Lys
        195                 200                 205 ctg gcc aaa gtg atg gaa aat tgg aca ccg ggt gct ccg aaa ccg aaa        672
Leu Ala Lys Val Met Glu Asn Trp Thr Pro Gly Ala Pro Lys Pro Lys
    210                 215                 220 ctg ctg tat acc att ccg aca ggt cag aat ccg acc ggc acc agc att        720
Leu Leu Tyr Thr Ile Pro Thr Gly Gln Asn Pro Thr Gly Thr Ser Ile
225                 230                 235                 240 gca gat cat cgt aaa gaa gcc atc tat aaa atc gcc cag aaa tac gat        768
Ala Asp His Arg Lys Glu Ala Ile Tyr Lys Ile Ala Gln Lys Tyr Asp
                245                 250                 255 ttc ctg atc gtt gaa gat gag ccg tat tat ttc ctg cag atg aac ccg        816
Phe Leu Ile Val Glu Asp Glu Pro Tyr Tyr Phe Leu Gln Met Asn Pro
            260                 265                 270 tat atc aaa gat ctg aaa gaa cgt gaa aaa gca cag agc agt ccg aaa        864
Tyr Ile Lys Asp Leu Lys Glu Arg Glu Lys Ala Gln Ser Ser Pro Lys
        275                 280                 285 cag gat cat gat gaa ttt ctg aaa agc ctg gcc aat acc ttt ctg agc        912
Gln Asp His Asp Glu Phe Leu Lys Ser Leu Ala Asn Thr Phe Leu Ser
    290                 295                 300 ctg gat acc gaa ggt cgt gtt att cgt atg gat agc ttt tca aaa gtt        960
Leu Asp Thr Glu Gly Arg Val Ile Arg Met Asp Ser Phe Ser Lys Val
305                 310                 315                 320 ctg gca ccg ggt aca cgt ctg ggt tgg att acc ggt agc agc aaa att       1008
Leu Ala Pro Gly Thr Arg Leu Gly Trp Ile Thr Gly Ser Ser Lys Ile
                325                 330                 335 ctg aaa ccg tat ctg agt ctg cat gaa atg acc att cag gca ccg gca       1056
Leu Lys Pro Tyr Leu Ser Leu His Glu Met Thr Ile Gln Ala Pro Ala
            340                 345                 350 ggt ttt acc cag gtt ctg gtt aat gca acc ctg agc cgt tgg ggt cag       1104
Gly Phe Thr Gln Val Leu Val Asn Ala Thr Leu Ser Arg Trp Gly Gln
        355                 360                 365 aaa ggc tat ctg gat tgg ctg ctg ggt ctg cgt cat gaa tat acc ctg       1152
Lys Gly Tyr Leu Asp Trp Leu Leu Gly Leu Arg His Glu Tyr Thr Leu
    370                 375                 380 aaa cgt gat tgt gca att gat gcc ctg tat aaa tac ctg ccg cag agt       1200
Lys Arg Asp Cys Ala Ile Asp Ala Leu Tyr Lys Tyr Leu Pro Gln Ser
385                 390                 395                 400 gat gca ttt gtt att aat ccg cct att gcc ggt atg ttc ttt acc gtt       1248
Asp Ala Phe Val Ile Asn Pro Pro Ile Ala Gly Met Phe Phe Thr Val
                405                 410                 415 aat att gat gca agc gtg cac ccg gaa ttc aaa acc aaa tat aac agc       1296
Asn Ile Asp Ala Ser Val His Pro Glu Phe Lys Thr Lys Tyr Asn Ser
            420                 425                 430 gat ccg tat cag ctg gaa cag agc ctg tat cat aaa gtt gtt gaa cgt       1344
Asp Pro Tyr Gln Leu Glu Gln Ser Leu Tyr His Lys Val Val Glu Arg
        435                 440                 445 ggt gtt ctg gtt gtt ccg ggt agc tgg ttt aaa agc gaa ggt gaa acc       1392
Gly Val Leu Val Val Pro Gly Ser Trp Phe Lys Ser Glu Gly Glu Thr
    450                 455                 460 gaa ccg cct cag cct gca gaa agt aaa gaa gtt agc aat ccg aat att       1440
Glu Pro Pro Gln Pro Ala Glu Ser Lys Glu Val Ser Asn Pro Asn Ile
465                 470                 475                 480 atc ttc ttc cgt ggc acc tat gca gca gtg agc cct gaa aaa ctg acc       1488
Ile Phe Phe Arg Gly Thr Tyr Ala Ala Val Ser Pro Glu Lys Leu Thr
                485                 490                 495
```

```
gaa ggc ctg aaa cgc ctg ggt gat acc ctg tat gaa gaa ttt ggt atc    1536
Glu Gly Leu Lys Arg Leu Gly Asp Thr Leu Tyr Glu Glu Phe Gly Ile
            500                 505                 510 agc aaa taa gctt                                                   1549
Ser Lys
```

<210> SEQ ID NO 10
<211> LENGTH: 514
<212> TYPE: PRT
<213> ORGANISM: Saccharomyces cerevisiae

<400> SEQUENCE: 10

```
Met Ala Ser Arg Gly Ser His His His His His Gly Ala Met Thr
1               5                   10                  15

Leu Pro Glu Ser Lys Asp Phe Ser Tyr Leu Phe Ser Asp Glu Thr Asn
                20                  25                  30

Ala Arg Lys Pro Ser Pro Leu Lys Thr Cys Ile His Leu Phe Gln Asp
            35                  40                  45

Pro Asn Ile Ile Phe Leu Gly Gly Leu Pro Leu Lys Asp Tyr Phe
    50                  55                  60

Pro Trp Asp Asn Leu Ser Val Asp Ser Pro Lys Pro Pro Phe Pro Gln
65                  70                  75                  80

Gly Ile Gly Ala Pro Ile Asp Glu Gln Asn Cys Ile Lys Tyr Thr Val
                85                  90                  95

Asn Lys Asp Tyr Ala Asp Lys Ser Ala Asn Pro Ser Asn Asp Ile Pro
            100                 105                 110

Leu Ser Arg Ala Leu Gln Tyr Gly Phe Ser Ala Gly Gln Pro Glu Leu
        115                 120                 125

Leu Asn Phe Ile Arg Asp His Thr Lys Ile Ile His Asp Leu Lys Tyr
    130                 135                 140

Lys Asp Trp Asp Val Leu Ala Thr Ala Gly Asn Thr Asn Ala Trp Glu
145                 150                 155                 160

Ser Thr Leu Arg Val Phe Cys Asn Arg Gly Asp Val Ile Leu Val Glu
                165                 170                 175

Ala His Ser Phe Ser Ser Leu Ala Ser Ala Glu Ala Gln Gly Val
            180                 185                 190

Ile Thr Phe Pro Val Pro Ile Asp Ala Asp Gly Ile Ile Pro Glu Lys
        195                 200                 205

Leu Ala Lys Val Met Glu Asn Trp Thr Pro Gly Ala Pro Lys Pro Lys
    210                 215                 220

Leu Leu Tyr Thr Ile Pro Thr Gly Gln Asn Pro Thr Gly Thr Ser Ile
225                 230                 235                 240

Ala Asp His Arg Lys Glu Ala Ile Tyr Lys Ile Ala Gln Lys Tyr Asp
                245                 250                 255

Phe Leu Ile Val Glu Asp Glu Pro Tyr Tyr Phe Leu Gln Met Asn Pro
            260                 265                 270

Tyr Ile Lys Asp Leu Lys Glu Arg Glu Lys Ala Gln Ser Ser Pro Lys
        275                 280                 285

Gln Asp His Asp Glu Phe Leu Lys Ser Leu Ala Asn Thr Phe Leu Ser
    290                 295                 300

Leu Asp Thr Glu Gly Arg Val Ile Arg Met Asp Ser Phe Ser Lys Val
305                 310                 315                 320

Leu Ala Pro Gly Thr Arg Leu Gly Trp Ile Thr Gly Ser Ser Lys Ile
                325                 330                 335
```

```
Leu Lys Pro Tyr Leu Ser Leu His Glu Met Thr Ile Gln Ala Pro Ala
            340                 345                 350

Gly Phe Thr Gln Val Leu Val Asn Ala Thr Leu Ser Arg Trp Gly Gln
        355                 360                 365

Lys Gly Tyr Leu Asp Trp Leu Leu Gly Leu Arg His Glu Tyr Thr Leu
370                 375                 380

Lys Arg Asp Cys Ala Ile Asp Ala Leu Tyr Lys Tyr Leu Pro Gln Ser
385                 390                 395                 400

Asp Ala Phe Val Ile Asn Pro Pro Ile Ala Gly Met Phe Phe Thr Val
                405                 410                 415

Asn Ile Asp Ala Ser Val His Pro Glu Phe Lys Thr Lys Tyr Asn Ser
            420                 425                 430

Asp Pro Tyr Gln Leu Glu Gln Ser Leu Tyr His Lys Val Val Glu Arg
        435                 440                 445

Gly Val Leu Val Val Pro Gly Ser Trp Phe Lys Ser Glu Gly Glu Thr
    450                 455                 460

Glu Pro Pro Gln Pro Ala Glu Ser Lys Glu Val Ser Asn Pro Asn Ile
465                 470                 475                 480

Ile Phe Phe Arg Gly Thr Tyr Ala Ala Val Ser Pro Glu Lys Leu Thr
                485                 490                 495

Glu Gly Leu Lys Arg Leu Gly Asp Thr Leu Tyr Glu Glu Phe Gly Ile
            500                 505                 510

Ser Lys

<210> SEQ ID NO 11
<211> LENGTH: 1141
<212> TYPE: DNA
<213> ORGANISM: Bacillus sphaericus
<220> FEATURE:
<221> NAME/KEY: CDS
<222> LOCATION: (1)..(1137)
<223> OTHER INFORMATION: sequence of leudh of Bacillus sphaericus
      optimized for the codon usage of Escherichia coli with an amino-
      terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1136)..(1141)
<223> OTHER INFORMATION: HindIII restriction site

```
                        85                  90                  95
att att ggt gat ccg ttc aaa gat aaa aac gaa gaa atg ttt cgt gcc    336
Ile Ile Gly Asp Pro Phe Lys Asp Lys Asn Glu Glu Met Phe Arg Ala
            100                 105                 110 ctg ggt cgt ttt att cag ggt ctg aat ggt cgt tat att acc gca gaa    384
Leu Gly Arg Phe Ile Gln Gly Leu Asn Gly Arg Tyr Ile Thr Ala Glu
        115                 120                 125 gat gtt ggc acc acc gtt ctg gat atg gat ctg att cat gaa gaa acc    432
Asp Val Gly Thr Thr Val Leu Asp Met Asp Leu Ile His Glu Glu Thr
130                 135                 140 acc tat gtg acc ggt att agt ccg gca ttt ggt agc agc ggt aat ccg    480
Thr Tyr Val Thr Gly Ile Ser Pro Ala Phe Gly Ser Ser Gly Asn Pro
145                 150                 155                 160 agt ccg gtt acc gcc tat ggt gtt tat cgt ggc atg aaa gca gca gca    528
Ser Pro Val Thr Ala Tyr Gly Val Tyr Arg Gly Met Lys Ala Ala Ala
            165                 170                 175 aaa gaa gcc ttt ggt agc gat agc ctg gaa ggc ctg aaa gtt agc gtg    576
Lys Glu Ala Phe Gly Ser Asp Ser Leu Glu Gly Leu Lys Val Ser Val
                180                 185                 190 cag ggt ctg ggt aat gtt gca tat aaa ctg tgt gaa tat ctg cac aac    624
Gln Gly Leu Gly Asn Val Ala Tyr Lys Leu Cys Glu Tyr Leu His Asn
            195                 200                 205 gaa ggt gca aaa ctg gtt gtt acc gat att aat cag gca gcc att gat    672
Glu Gly Ala Lys Leu Val Val Thr Asp Ile Asn Gln Ala Ala Ile Asp
210                 215                 220 cgt gtg gtg aat gat ttt gat gca att gcc gtt gca ccg gat gaa att    720
Arg Val Val Asn Asp Phe Asp Ala Ile Ala Val Ala Pro Asp Glu Ile
225                 230                 235                 240 tat gca caa gaa gtg gat atc ttt agc ccg tgt gcg ctg ggt gca att    768
Tyr Ala Gln Glu Val Asp Ile Phe Ser Pro Cys Ala Leu Gly Ala Ile
                245                 250                 255 ctg aat gat gaa acc att ccg cag ctg aaa gca aaa gtt att gcc ggt    816
Leu Asn Asp Glu Thr Ile Pro Gln Leu Lys Ala Lys Val Ile Ala Gly
            260                 265                 270 agc gca aat aac caa ctg aaa gat agc cgt cat ggt gat tat ctg cat    864
Ser Ala Asn Asn Gln Leu Lys Asp Ser Arg His Gly Asp Tyr Leu His
        275                 280                 285 gag ctg ggt att gtt tat gct ccg gat tat gtt att aat gcc ggt ggt    912
Glu Leu Gly Ile Val Tyr Ala Pro Asp Tyr Val Ile Asn Ala Gly Gly
290                 295                 300 gtg att aat gtt gcc gat gaa ctg tat ggt tat aat cgt gaa cgt gcc    960
Val Ile Asn Val Ala Asp Glu Leu Tyr Gly Tyr Asn Arg Glu Arg Ala
305                 310                 315                 320 atg aaa cgt gtg gat ggt att tat gat agc atc gag aaa atc ttt gcc    1008
Met Lys Arg Val Asp Gly Ile Tyr Asp Ser Ile Glu Lys Ile Phe Ala
                325                 330                 335 atc agc aaa cgt gat ggt att ccg acc tat gtt gca gca aat cgt ctg    1056
Ile Ser Lys Arg Asp Gly Ile Pro Thr Tyr Val Ala Ala Asn Arg Leu
            340                 345                 350 gcc gaa gaa cgt att gca cgt gtt gca aaa agc cgt agc cag ttt ctg    1104
Ala Glu Glu Arg Ile Ala Arg Val Ala Lys Ser Arg Ser Gln Phe Leu
        355                 360                 365 aaa aac gaa aaa aac att ctg aac ggt cgt taa gctt                   1141
Lys Asn Glu Lys Asn Ile Leu Asn Gly Arg
370                 375

<210> SEQ ID NO 12
<211> LENGTH: 378
<212> TYPE: PRT
<213> ORGANISM: Bacillus sphaericus
```

<400> SEQUENCE: 12

```
Met Ala Ser Arg Gly Ser His His His His His Gly Ala Met Glu
1               5                   10                  15

Ile Phe Lys Tyr Met Glu Lys Tyr Asp Tyr Glu Gln Leu Val Phe Cys
                20                  25                  30

Gln Asp Glu Ala Ser Gly Leu Lys Ala Val Ile Ala Ile His Asp Thr
            35                  40                  45

Thr Leu Gly Pro Ala Leu Gly Ala Arg Met Trp Thr Tyr Ala Ser
        50                  55                  60

Glu Glu Asn Ala Ile Glu Asp Ala Leu Arg Leu Ala Arg Gly Met Thr
65                  70                  75                  80

Tyr Lys Asn Ala Ala Ala Gly Leu Asn Leu Gly Gly Lys Thr Val
                85                  90                  95

Ile Ile Gly Asp Pro Phe Lys Asp Lys Asn Glu Glu Met Phe Arg Ala
                100                 105                 110

Leu Gly Arg Phe Ile Gln Gly Leu Asn Gly Arg Tyr Ile Thr Ala Glu
            115                 120                 125

Asp Val Gly Thr Thr Val Leu Asp Met Asp Leu Ile His Glu Glu Thr
        130                 135                 140

Thr Tyr Val Thr Gly Ile Ser Pro Ala Phe Gly Ser Ser Gly Asn Pro
145                 150                 155                 160

Ser Pro Val Thr Ala Tyr Gly Val Tyr Arg Gly Met Lys Ala Ala Ala
                165                 170                 175

Lys Glu Ala Phe Gly Ser Asp Ser Leu Glu Gly Leu Lys Val Ser Val
            180                 185                 190

Gln Gly Leu Gly Asn Val Ala Tyr Lys Leu Cys Glu Tyr Leu His Asn
        195                 200                 205

Glu Gly Ala Lys Leu Val Val Thr Asp Ile Asn Gln Ala Ala Ile Asp
210                 215                 220

Arg Val Val Asn Asp Phe Asp Ala Ile Ala Val Ala Pro Asp Glu Ile
225                 230                 235                 240

Tyr Ala Gln Glu Val Asp Ile Phe Ser Pro Cys Ala Leu Gly Ala Ile
                245                 250                 255

Leu Asn Asp Glu Thr Ile Pro Gln Leu Lys Ala Lys Val Ile Ala Gly
            260                 265                 270

Ser Ala Asn Asn Gln Leu Lys Asp Ser Arg His Gly Asp Tyr Leu His
        275                 280                 285

Glu Leu Gly Ile Val Tyr Ala Pro Asp Tyr Val Ile Asn Ala Gly Gly
    290                 295                 300

Val Ile Asn Val Ala Asp Glu Leu Tyr Gly Tyr Asn Arg Glu Arg Ala
305                 310                 315                 320

Met Lys Arg Val Asp Gly Ile Tyr Asp Ser Ile Glu Lys Ile Phe Ala
                325                 330                 335

Ile Ser Lys Arg Asp Gly Ile Pro Thr Tyr Val Ala Ala Asn Arg Leu
            340                 345                 350

Ala Glu Glu Arg Ile Ala Arg Val Ala Lys Ser Arg Ser Gln Phe Leu
        355                 360                 365

Lys Asn Glu Lys Asn Ile Leu Asn Gly Arg
370                 375
```

<210> SEQ ID NO 13
<211> LENGTH: 1147
<212> TYPE: DNA

```
<213> ORGANISM: Thermoactinomyces intermedius
<220> FEATURE:
<221> NAME/KEY: CDS
<222> LOCATION: (1)..(1143)
<223> OTHER INFORMATION: sequence of phedh of Thermoactinomyces
      intermedius optimized for the codon usage of Escherichia coli with
      an amino-terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1142)..(1147)
<223> OTHER INFORMATION: HindIII restriction site

<400> SEQUENCE: 13
```

| atg | gct | agc | aga | gga | tcg | cat | cac | cat | cac | cat | cac | ggc | gcc | atg | cgt | 48 |
|---|---|---|---|---|---|---|---|---|---|---|---|---|---|---|---|---|
| Met | Ala | Ser | Arg | Gly | Ser | His | His | His | His | His | His | Gly | Ala | Met | Arg | |
| 1 | | | | 5 | | | | | 10 | | | | | 15 | | |

| gat | gtt | ttt | gaa | atg | atg | gat | cgt | tat | ggt | cac | gaa | cag | gtg | att | ttt | 96 |
|---|---|---|---|---|---|---|---|---|---|---|---|---|---|---|---|---|
| Asp | Val | Phe | Glu | Met | Met | Asp | Arg | Tyr | Gly | His | Glu | Gln | Val | Ile | Phe | |
| | | | 20 | | | | | 25 | | | | | 30 | | | |

| tgt | cgt | cat | ccg | cag | aca | ggt | ctg | aaa | gca | att | att | gca | ctg | cat | aat | 144 |
|---|---|---|---|---|---|---|---|---|---|---|---|---|---|---|---|---|
| Cys | Arg | His | Pro | Gln | Thr | Gly | Leu | Lys | Ala | Ile | Ile | Ala | Leu | His | Asn | |
| | | 35 | | | | | 40 | | | | | 45 | | | | |

| acc | acc | gca | ggt | ccg | gca | ctg | ggt | ggt | tgt | cgt | atg | att | ccg | tat | gca | 192 |
|---|---|---|---|---|---|---|---|---|---|---|---|---|---|---|---|---|
| Thr | Thr | Ala | Gly | Pro | Ala | Leu | Gly | Gly | Cys | Arg | Met | Ile | Pro | Tyr | Ala | |
| 50 | | | | | 55 | | | | | 60 | | | | | | |

| agc | acc | gat | gaa | gca | ctg | gaa | gat | gtt | ctg | cgt | ctg | agc | aaa | ggt | atg | 240 |
|---|---|---|---|---|---|---|---|---|---|---|---|---|---|---|---|---|
| Ser | Thr | Asp | Glu | Ala | Leu | Glu | Asp | Val | Leu | Arg | Leu | Ser | Lys | Gly | Met | |
| 65 | | | | 70 | | | | | 75 | | | | | 80 | | |

| acc | tat | aaa | tgt | agc | ctg | gcc | gat | gtt | gat | ttt | ggt | ggt | ggt | aaa | atg | 288 |
|---|---|---|---|---|---|---|---|---|---|---|---|---|---|---|---|---|
| Thr | Tyr | Lys | Cys | Ser | Leu | Ala | Asp | Val | Asp | Phe | Gly | Gly | Gly | Lys | Met | |
| | | | 85 | | | | | 90 | | | | | 95 | | | |

| gtg | att | att | ggc | gat | ccg | aaa | aaa | gac | aaa | agt | ccg | gaa | ctg | ttt | cgt | 336 |
|---|---|---|---|---|---|---|---|---|---|---|---|---|---|---|---|---|
| Val | Ile | Ile | Gly | Asp | Pro | Lys | Lys | Asp | Lys | Ser | Pro | Glu | Leu | Phe | Arg | |
| | | 100 | | | | | 105 | | | | | 110 | | | | |

| gtg | att | ggt | cgt | ttt | gtt | ggt | ggt | ctg | aat | ggt | cgc | ttt | tat | acc | ggc | 384 |
|---|---|---|---|---|---|---|---|---|---|---|---|---|---|---|---|---|
| Val | Ile | Gly | Arg | Phe | Val | Gly | Gly | Leu | Asn | Gly | Arg | Phe | Tyr | Thr | Gly | |
| | 115 | | | | | 120 | | | | | 125 | | | | | |

| acc | gat | atg | ggc | acc | aat | ccg | gaa | gat | ttt | gtt | cat | gca | gca | cgt | gaa | 432 |
|---|---|---|---|---|---|---|---|---|---|---|---|---|---|---|---|---|
| Thr | Asp | Met | Gly | Thr | Asn | Pro | Glu | Asp | Phe | Val | His | Ala | Ala | Arg | Glu | |
| 130 | | | | | 135 | | | | | 140 | | | | | | |

| agc | aaa | agt | ttt | gca | ggt | ctg | ccg | aaa | agc | tat | ggt | ggc | aaa | ggt | gat | 480 |
|---|---|---|---|---|---|---|---|---|---|---|---|---|---|---|---|---|
| Ser | Lys | Ser | Phe | Ala | Gly | Leu | Pro | Lys | Ser | Tyr | Gly | Gly | Lys | Gly | Asp | |
| 145 | | | | 150 | | | | | 155 | | | | | 160 | | |

| acc | agc | att | ccg | acc | gca | ctg | ggc | gtt | ttt | cat | ggt | atg | cgt | gca | acc | 528 |
|---|---|---|---|---|---|---|---|---|---|---|---|---|---|---|---|---|
| Thr | Ser | Ile | Pro | Thr | Ala | Leu | Gly | Val | Phe | His | Gly | Met | Arg | Ala | Thr | |
| | | | 165 | | | | | 170 | | | | | 175 | | | |

| gca | cgt | ttt | ctg | tgg | ggc | acc | gat | cag | ctg | aaa | ggt | cgt | gtt | gtt | gca | 576 |
|---|---|---|---|---|---|---|---|---|---|---|---|---|---|---|---|---|
| Ala | Arg | Phe | Leu | Trp | Gly | Thr | Asp | Gln | Leu | Lys | Gly | Arg | Val | Val | Ala | |
| | | | 180 | | | | | 185 | | | | | 190 | | | |

| att | cag | ggt | gtt | ggt | aaa | gtt | ggt | gaa | cgt | ctg | ctg | cag | ctg | ctg | gtt | 624 |
|---|---|---|---|---|---|---|---|---|---|---|---|---|---|---|---|---|
| Ile | Gln | Gly | Val | Gly | Lys | Val | Gly | Glu | Arg | Leu | Leu | Gln | Leu | Leu | Val | |
| | | 195 | | | | | 200 | | | | | 205 | | | | |

| gaa | gtt | ggt | gca | tat | tgt | aaa | att | gcc | gat | att | gat | agc | gtt | cgt | tgc | 672 |
|---|---|---|---|---|---|---|---|---|---|---|---|---|---|---|---|---|
| Glu | Val | Gly | Ala | Tyr | Cys | Lys | Ile | Ala | Asp | Ile | Asp | Ser | Val | Arg | Cys | |
| 210 | | | | | 215 | | | | | 220 | | | | | | |

| gag | caa | ctg | aaa | gaa | aaa | tat | ggt | gat | aaa | gtg | cag | ctg | gtt | gat | gtg | 720 |
|---|---|---|---|---|---|---|---|---|---|---|---|---|---|---|---|---|
| Glu | Gln | Leu | Lys | Glu | Lys | Tyr | Gly | Asp | Lys | Val | Gln | Leu | Val | Asp | Val | |
| 225 | | | | 230 | | | | | 235 | | | | | 240 | | |

| aac | cgt | att | cat | aaa | gaa | agc | tgc | gat | atc | ttt | agc | ccg | tgt | gca | aaa | 768 |
|---|---|---|---|---|---|---|---|---|---|---|---|---|---|---|---|---|
| Asn | Arg | Ile | His | Lys | Glu | Ser | Cys | Asp | Ile | Phe | Ser | Pro | Cys | Ala | Lys | |

```
                Asn Arg Ile His Lys Glu Ser Cys Asp Ile Phe Ser Pro Cys Ala Lys
                                245                 250                 255 gt ggt gtg gtt aat gat gat acc att gat gaa ttt cgt tgc ctg gca          816
Gly Gly Val Val Asn Asp Asp Thr Ile Asp Glu Phe Arg Cys Leu Ala
                260                 265                 270 att gtt ggt agc gca aat aat cag ctg gta gaa gat cgt cat ggt gca         864
Ile Val Gly Ser Ala Asn Asn Gln Leu Val Glu Asp Arg His Gly Ala
                275                 280                 285 ctg ctg cag aaa cgt agc att tgt tat gca ccg gat tat ctg gtt aat         912
Leu Leu Gln Lys Arg Ser Ile Cys Tyr Ala Pro Asp Tyr Leu Val Asn
                290                 295                 300 gca ggc ggt ctg att cag gtt gca gat gaa ctg gaa ggt ttt cat gaa         960
Ala Gly Gly Leu Ile Gln Val Ala Asp Glu Leu Glu Gly Phe His Glu
305                 310                 315                 320 gaa cgt gtt ctg gca aaa acc gaa gcc att tat gat atg gtg ctg gat        1008
Glu Arg Val Leu Ala Lys Thr Glu Ala Ile Tyr Asp Met Val Leu Asp
                325                 330                 335 att ttt cac cgt gcc aaa aac gaa aac att acc acc tgt gaa gca gcc        1056
Ile Phe His Arg Ala Lys Asn Glu Asn Ile Thr Thr Cys Glu Ala Ala
                340                 345                 350 gat cgt att gtt atg gaa cgt ctg aaa aaa ctg acc gat att cgt cgt        1104
Asp Arg Ile Val Met Glu Arg Leu Lys Lys Leu Thr Asp Ile Arg Arg
                355                 360                 365 att ctg ctg gaa gat ccg cgt aat agc gca cgt cgt taa gctt             1147
Ile Leu Leu Glu Asp Pro Arg Asn Ser Ala Arg Arg
                370                 375                 380

<210> SEQ ID NO 14
<211> LENGTH: 380
<212> TYPE: PRT
<213> ORGANISM: Thermoactinomyces intermedius

<400> SEQUENCE: 14

Met Ala Ser Arg Gly Ser His His His His His Gly Ala Met Arg
1               5                   10                  15

Asp Val Phe Glu Met Met Asp Arg Tyr Gly His Glu Gln Val Ile Phe
                20                  25                  30

Cys Arg His Pro Gln Thr Gly Leu Lys Ala Ile Ala Leu His Asn
            35                  40                  45

Thr Thr Ala Gly Pro Ala Leu Gly Gly Cys Arg Met Ile Pro Tyr Ala
50                  55                  60

Ser Thr Asp Glu Ala Leu Glu Asp Val Leu Arg Leu Ser Lys Gly Met
65                  70                  75                  80

Thr Tyr Lys Cys Ser Leu Ala Asp Val Asp Phe Gly Gly Lys Met
                85                  90                  95

Val Ile Ile Gly Asp Pro Lys Lys Asp Lys Ser Pro Glu Leu Phe Arg
                100                 105                 110

Val Ile Gly Arg Phe Val Gly Gly Leu Asn Gly Arg Phe Tyr Thr Gly
            115                 120                 125

Thr Asp Met Gly Thr Asn Pro Glu Asp Phe Val His Ala Ala Arg Glu
            130                 135                 140

Ser Lys Ser Phe Ala Gly Leu Pro Lys Ser Tyr Gly Gly Lys Gly Asp
145                 150                 155                 160

Thr Ser Ile Pro Thr Ala Leu Gly Val Phe His Gly Met Arg Ala Thr
                165                 170                 175

Ala Arg Phe Leu Trp Gly Thr Asp Gln Leu Lys Gly Arg Val Val Ala
                180                 185                 190
```

-continued

```
Ile Gln Gly Val Gly Lys Val Gly Glu Arg Leu Leu Gln Leu Leu Val
            195                 200                 205

Glu Val Gly Ala Tyr Cys Lys Ile Ala Asp Ile Asp Ser Val Arg Cys
            210                 215                 220

Glu Gln Leu Lys Glu Lys Tyr Gly Asp Lys Val Gln Leu Val Asp Val
225                 230                 235                 240

Asn Arg Ile His Lys Glu Ser Cys Asp Ile Phe Ser Pro Cys Ala Lys
                245                 250                 255

Gly Gly Val Val Asn Asp Asp Thr Ile Asp Glu Phe Arg Cys Leu Ala
            260                 265                 270

Ile Val Gly Ser Ala Asn Asn Gln Leu Val Glu Asp Arg His Gly Ala
            275                 280                 285

Leu Leu Gln Lys Arg Ser Ile Cys Tyr Ala Pro Asp Tyr Leu Val Asn
            290                 295                 300

Ala Gly Gly Leu Ile Gln Val Ala Asp Glu Leu Glu Gly Phe His Glu
305                 310                 315                 320

Glu Arg Val Leu Ala Lys Thr Glu Ala Ile Tyr Asp Met Val Leu Asp
                325                 330                 335

Ile Phe His Arg Ala Lys Asn Glu Asn Ile Thr Thr Cys Glu Ala Ala
            340                 345                 350

Asp Arg Ile Val Met Glu Arg Leu Lys Lys Leu Thr Asp Ile Arg Arg
            355                 360                 365

Ile Leu Leu Glu Asp Pro Arg Asn Ser Ala Arg Arg
            370                 375                 380
```